United States Patent
Gerdes et al.

(10) Patent No.: US 9,499,472 B2
(45) Date of Patent: Nov. 22, 2016

(54) ASPARTYLAMIDE INHIBITORS OF EXCITATORY AMINO ACID TRANSPORTERS

(71) Applicant: THE UNIVERSITY OF MONTANA, Missoula, MT (US)

(72) Inventors: John M. Gerdes, Coos Bay, OR (US); Richard J. Bridges, Missoula, MT (US); Syed K. Ahmed, Hyderabad (IN); Sarjubhai Patel, Missoula, MT (US)

(73) Assignee: THE UNIVERSITY OF MONTANA, Missoula, MT (US)

(*) Notice: Subject to any disclaimer, the term of this patent is extended or adjusted under 35 U.S.C. 154(b) by 0 days.

(21) Appl. No.: 14/382,508

(22) PCT Filed: Mar. 5, 2013

(86) PCT No.: PCT/US2013/029080
§ 371 (c)(1),
(2) Date: Sep. 2, 2014

(87) PCT Pub. No.: WO2013/134241
PCT Pub. Date: Sep. 12, 2013

(65) Prior Publication Data
US 2015/0023878 A1  Jan. 22, 2015

Related U.S. Application Data

(60) Provisional application No. 61/606,782, filed on Mar. 5, 2012.

(51) Int. Cl.
| | | |
|---|---|---|
| A61K 51/00 | (2006.01) |
| A61M 36/14 | (2006.01) |
| C07C 69/635 | (2006.01) |
| C07C 237/04 | (2006.01) |
| C07B 59/00 | (2006.01) |
| A61K 51/04 | (2006.01) |
| C07C 67/317 | (2006.01) |
| C07F 7/22 | (2006.01) |

(52) U.S. Cl.
CPC ............ *C07C 69/635* (2013.01); *A61K 51/04* (2013.01); *C07B 59/001* (2013.01); *C07C 67/317* (2013.01); *C07C 237/04* (2013.01); *C07F 7/2212* (2013.01); *C07B 2200/05* (2013.01); *C07C 2103/18* (2013.01)

(58) Field of Classification Search
CPC ............ C07C 69/635; C07C 237/04; C07C 2103/18; C07C 67/317; C07B 2200/05; C07B 59/001; A61K 51/04; C07F 7/2212
USPC ...................................................... 424/1.89
See application file for complete search history.

(56) References Cited

U.S. PATENT DOCUMENTS

| | | | |
|---|---|---|---|
| 6,417,397 B1* | 7/2002 | Goodman et al. ............. 564/123 |
| 2003/0022930 A1 | 1/2003 | Stack et al. | |
| 2006/0100465 A1 | 5/2006 | Kabalka | |
| 2007/0142467 A1* | 6/2007 | Esslinger et al. ............. 514/520 |
| 2008/0248485 A1* | 10/2008 | Shimamoto et al. .......... 435/7.1 |
| 2010/0292478 A1 | 11/2010 | Cho et al. | |
| 2011/0184159 A1 | 7/2011 | Friebe et al. | |

OTHER PUBLICATIONS

Greenfield et al. Bioorg. Med. Chem. Lett. 15 (2005) 4985-4988.*
Hess et al. Appl. Rad. Isot. 57 (2002) 185-191.*
Nuijens et al. (Tetrahedron Lett.) 50 (2009) 2719-2721.*
Pike et al. J. Chem. Soc., Perkin Trans. 1, 1999, 245-248.*
Ametamey et al., "Molecular Imaging with PET," Chem. Rev. 108:1501-1516 (2008).
Aoki et al., "Mutations in the Glutamate Transporter EAAT2 Gene Do Not Cause Abnormal EAAT2 Transcripts in Amyotrophic Lateral Sclerosis," Ann. Neurol. 43:645-653 (1998).
Berger et al., "Comparative Analysis of Glutamate Transporter Expression in Rat Brain Using Differential Double In Situ Hybridization," Ant. Embryol. 198(1):13-30 (1998).
Bristol et al., "Glutamate Transporter Gene Expression in Amyotrophic Lateral Sclerosis Motor Cortex," Ann. Neurol. 39(5):676-679 (1996).

(Continued)

*Primary Examiner* — Michael G Hartley
*Assistant Examiner* — Sean R Donohue
(74) *Attorney, Agent, or Firm* — Minerva, PLLC; Zachary A. Scott

(57) ABSTRACT

The compounds of the invention are inhibitors of excitatory amino acid transporters (EAAT) that penetrate the blood-brain barrier to access the central nervous system. The compounds of the invention follow the structural formula:

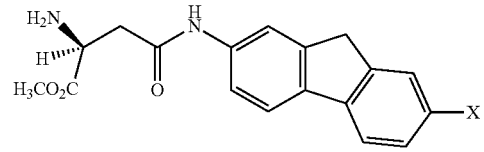

or a salt, ester or prodrug thereof, wherein X is a halogen, such as fluorine, or a radionuclide, such as fluorine-18. The compounds and methods described herein can be used for the treatment of, e.g., neurodegenerative disorders (e.g., amyotrophic lateral sclerosis), ischemia, spinal cord injury, and traumatic brain injury in a patient (e.g., a human). The invention further provides compounds and methods for the synthesis and use of radiographic tracers to diagnose and follow the progression of such disorders.

8 Claims, 14 Drawing Sheets

(56) References Cited

OTHER PUBLICATIONS

Cai et al., "Chemistry with [$^{18}$F]Fluoride Ion," *Eur. J. Org. Chem.* 17:2853-2873 (2008).
Chernet et al., "Use of LC/MS to Assess Brain Tracer Distribution in Preclinical, In Vivo Receptor Occupancy Studies: Dopamine D2, Serotonin 2A and NK-1 Receptors as Examples," *Life Sci.* 78:340-346 (2005).
Damont et al., "Radiosynthesis of [$^{18}$F]DPA-714, A Selective Radioligand for Imaging the Translocator Protein (18 kDa) with PET," *J. Label. Compds Radiopharm.* 51:286-292 (2008).
Danbolt, "Glutamate Uptake," *Prog. Neurobiol.* 65:1-105 (2001).
Ding et al., "PET Imaging of Norepinephrine Transporters," *Curr. Pharma. Design* 12:3831-3845 (2006).
Dollé et al., "Fluorine-18-Labelled Fluoropyridines: Advances in Radiopharmaceutical Design," *Curr. Pharm. Design* 11(25):3221-3235 (2005).
Dollé et al., "One-step radiosynthesis of [$^{18}$F]LBT-999: A Selective Radioligand for the Visualization of the Dopamine Transporter with PET," *J. Label. Compds Radiopharm.* 50:716-723 (2007).
Dollé et al., "Synthesis, Radiosynthesis and In Vivo Preliminary Evaluation of [$^{11}$C]LBT-999, a Selective Radioligand for the Visualisation of the Dopamine Transporter with PET," *Bioorg. Med. Chem.* 14:1115-1125 (2006).
Dörwald, "Side Reactions in Organic Synthesis," Wiley-VCH Verlag GmbH & Co. KGaA, Weinheim; Preface (2005).
Eckelman et al., "Discussion of Targeting Proteins In Vivo: In Vitro Guidelines," *Nuc. Med. Biol.* 33:449-451 (2006).
Eckelman et al., "Targeting Proteins In Vivo: In Vitro Guidelines," *Nuc. Med. Biol.* 33:161-164 (2006).
Esslinger et al., "The Substituted Aspartate Analogue L-B-Threo-Benzyl-Aspartate Preferentially Inhibits the Neuronal Excitatory Amino Acid Transporter EAAT3," *Neuropharmacol.* 49(6):850-861 (2005).
Füchtner et al., "Efficient Synthesis of the $^{18}$F-labelled 3-O-methyl-6-[$^{18}$F]fluoro-L-DOPA," *App. Rad. Isotopes* 58:575-578 (2003).
Furuya et al., "Carbon—Fluorine Reductive Elimination from a High-Valent Palladium Fluoride," *J. Am Chem. Soc.* 130:10060-10061 (2008).
Furuya et al., "Mechanism of C—F Reductive Elimination from Palladium(IV) Fluorides," *J. Am. Chem. Soc.* 132:3793-3807 (2010).
Furuya et al., "Palladium-mediated Fluorination of Arylboronic Acids," *Angew. Chem. Int. Ed.* 47:5993-5996 (2008).
Goodwin et al., "In Silico Predictions of Blood-Brain Barrier Penetration: Considerations to 'Keep in Mind'," *J. Pharmacol Exp. Therapeu.* 315(2):477-483 (2005).
Huang et al., "Comparative Evaluation in Nonhuman Primates of Five PET Radiotracers for Imaging the Serotonin Transporters: [$^{11}$C]McN 5652, [$^{11}$C]ADAM, [$^{11}$C]DASB, [$^{11}$C]DAPA, and [$^{11}$C]AFM," *J. Cerebral Blood Flow Metabol.* 22:1377-1398 (2002).
Huang et al., "Development of Effective PET and SPECT Imaging Agents for the Serotonin Transporter: Has a Twenty-Year Journey Reached Its Destination?," *Curr. Top. Med. Chem.* 10(15):1499-1526 (2010).
Innis et al., "Consensus Nomenclature for In Vivo Imaging of Reversibly Binding Radioligands," *J. Cereb. Blood Flow Metab.* 27:1533-1539 (2007).
Kilbourn, "Fluorine-18 Labeling of Radiopharmaceuticals," Nuclear Science Series (Kilbourn M R Ed.), National Academy Press, Washington, D.C., 1-149 (1990).
Laruelle et al., "Positron Emission Tomography: Imaging and Quantification of Neurotransporter Availability," *Methods* 27:287-299 (2002).
Lasne et al., "Chemistry of $\beta^+$-Emitting Compounds Based on Fluorine-18," *Topics in Current Chemistry* 222:201-258 (2002).
Leary et al., "The Central Cavity in Trimeric Glutamate Transporters Restricts Ligand Diffusion," *PNAS* 108(36):14980-14985 (2011).
Lee et al., "A Fluoride-Derived Electrophilic Late-State Fluorination Reagent for PET Imaging," *Science* 334:639-642 (2011).
Lehre et al., "Differential Expression of Two Glial Glutamate Transporters in the Rat Brain: Quantitative and Immunocytochemical Observations," *J. Neurosci.* 15(3):1835-1853 (1995).
Lehre et al., "The Number of Glutamate Transporter Subtype Molecules at Glutamatergic Synapses: Chemical and Stereological Quantification in Young Adult Rat Brain," *J. Neurosci.* 18(2):8751-8757 (1998).
Lin et al., "Aberrant RNA Processing in a Neurodegenerative Disease: the Cause for Absent EAAT2, a Glutamate Transporter, in Amyotrophic Lateral Sclerosis," *Neuron* 20:589-602 (1998).
Loening et al., "AMIDE: A Free Software Tool for Multimodality Medical Image Analysis," *Mol. Imaging* 2:131-137 (2003).
Marek et al., "Transgenically Encoded Protein Photoinactivation (FlAsH-FALI): Acute Inactivation of Synaptotagmin I," *Neuron* 36:805-813 (2002).
Maziere et al., "Use of Bromine-76 and Iodine-123 Radiohalogenated Tracers in the Drug Development Process," *Curr. Pharm. Des.* 7:1931-1943 (2001).
Meyer et al., "Alternative Splicing of the Glutamate Transporter EAAT2 (GLT-1)," *Neurosci. Lett.* 241(1):68-70 (1998).
Meyer et al., "The EAAT2 (GLT-1) Gene in Motor Neuron Disease: Absence of Mutations in Amyotrophic Lateral Sclerosis and a Point Mutation in Patients With Hereditary Spastic Paraplegia," *J. Neurol. Neurosurg. Psych.* 65:594-596 (1998).
Rothstein et al., "Localization of Neuronal and Glial Glutamate Transporters," *Neuron* 13(3):713-725 (1994).
Sattler et al., "In Vivo Rodent Studies for Discovery of an Excitatory Amino Acid Transporter 2 (EAAT2, GLT-1) PET Imaging Tracer to Biomark ALS," Abstract, ALS Association Meeting, Washington D.C., Mar. 4-7, 2012.
Tai et al., "Performance Evaluation of the Micropet P4: A PET System Dedicated to Animal Imaging," *Phys. Med. Biol.* 46:1845-1862 (2001).
VanBrocklin et al., "A New Precursor for the Preparation of 6-[$^{18}$F]Fluoro-L-m-tyrosine ([$^{18}$F]FMT): Efficient Synthesis and Comparison of Radiolabeling," *Appl. Rad. Isotopes* 61:1289-1294 (2004).
Ye, "Mass Spectrometric Characterization and Fluorophore-Assisted Light Inactivation of Human Excitatory Amino Acid Transporter 2," Dissertation, The Univ. of Montana (Mar. 2009).

* cited by examiner

FIG. 8A

| Assay | Assay Abbr. | Radioligand | Kd (M) | Test Cpd. | Reference Compound | Ki (M) Ref. Cpd. | Activity |
|---|---|---|---|---|---|---|---|
| NEUROTRANSMITTER RELATED | | | | | | | |
| Glutamate, NMDA Agonist Site (Ionotropic) | NMDA | [3H]CGP 39653 | 7E-9 | 1 or 6 | NMDA | 5.02E-6 | No |
| Glutamate, NMDA Agonist Site (Ionotropic) | NMDA | [3H]CGP 39653 | 7E-9 | 1 or 6 | NMDA | 5.02E-6 | No |
| Glutamate, NMDA, Glycine (Stry-insens Site) (Ionot | GLYCINE | [3H]-MDL-105,519 | 2E-8 | 1 or 6 | MDL-105,519 | 2.47E-8 | No |
| Glutamate, NMDA, Glycine (Stry-insens Site) (Ionot | GLYCINE | [3H]-MDL-105,519 | 2E-8 | 1 or 6 | MDL-105,519 | 2.47E-8 | No |
| Glycine, Strychnine-sensitive | STRYCH | [3H]Strychnine | 2.8E-8 | 1 or 6 | Strychnine nitrate | 2.30E-8 | No |
| Glycine, Strychnine-sensitive | STRYCH | [3H]Strychnine | 2.8E-8 | 1 or 6 | Strychnine nitrate | 2.30E-8 | No |
| Histamine, H1 | H1 | [3H]Pyrilamine | 1.3E-9 | 1 or 6 | Triprolidine | 5.25E-9 | No |
| Histamine, H1 | H1 | [3H]Pyrilamine | 1.3E-9 | 1 or 6 | Triprolidine | 5.25E-9 | No |
| Histamine, H2 | H2 | [125I]-Aminopotentidine | 7E-10 | 1 or 6 | Tiotidine | 1.12E-8 | No |
| Histamine, H2 | H2 | [125I]-Aminopotentidine | 7E-10 | 1 or 6 | Tiotidine | 1.12E-8 | No |
| Histamine, H3 | H3 | [3H]N-a-MeHistamine | 3.7E-10 | 1 or 6 | N-a-Methylhistamine | 3.28E-10 | No |

FIG. 8B

| Assay | Assay Abbr. | Radioligand | Kd (M) | Test Cpd. | Reference Compound | Ki (M) Ref. Cpd. | Activity |
|---|---|---|---|---|---|---|---|
| Histamine, H3 | H3 | [3H]N-a-MeHistamine | 3.7E-10 | 1 or 6 | N-a-Methylhistamine | 3.28E-10 | No |
| Melatonin, Non-selective | MEL | [125I]-2-Iodomelatonin | 6.6E-11 | 1 or 6 | Melatonin | 6.79E-10 | No |
| Melatonin, Non-selective | MEL | [125I]-2-Iodomelatonin | 6.6E-11 | 1 or 6 | Melatonin | 6.79E-10 | No |
| Muscarinic, M1 (hr) | M1HR | [3H]Scopolamine, N-Methyl | 5E-11 | 1 or 6 | (-)Scopolamine, MeBr | 4.92E-11 | No |
| Muscarinic, M1 (hr) | M1HR | [3H]Scopolamine, N-Methyl | 5E-11 | 1 or 6 | (-)Scopolamine, MeBr | 4.92E-11 | No |
| Muscarinic, M2 (h) | M2 (h) | [3H]Scopolamine, N-Methyl | 2.9E-10 | 1 or 6 | (-)Scopolamine, MeBr | 2.54E-10 | No |
| Muscarinic, M2 (h) | M2 (h) | [3H]Scopolamine, N-Methyl | 2.9E-10 | 1 or 6 | (-)Scopolamine, MeBr | 2.24E-10 | No |
| Muscarinic, Non-selective, Central | M-NS, C | [3H]QNB | 1.0E-10 | 1 or 6 | Atropine sulfate | 1.57E-10 | No |
| Muscarinic, Non-selective, Central | M-NS, C | [3H]QNB | 1.0E-10 | 1 or 6 | Atropine sulfate | 1.57E-10 | No |
| Muscarinic, Non-selective, Peripheral | M-NS, P | [3H]QNB | 3E-10 | 1 or 6 | Atropine sulfate | 3.32E-10 | No |
| Muscarinic, Non-selective, Peripheral | M-NS, P | [3H]QNB | 3E-10 | 1 or 6 | Atropine sulfate | 3.32E-10 | No |
| Nicotinic, Neuronal (a-BnTx insensitive) | NICO | [3H]Epibatidine | 6.3E-11 | 1 or 6 | (+/-) Epibatidine | 6.40E-11 | No |
| Nicotinic, Neuronal (a-BnTx insensitive) | NICO | [3H]Epibatidine | 6.3E-11 | 1 or 6 | (+/-) Epibatidine | 6.40E-11 | No |

FIG. 8C

| Assay | Assay Abbr. | Radioligand | Kd (M) | Test Cpd. | Reference Compound | Ki (M) Ref. Cpd. | Activity |
|---|---|---|---|---|---|---|---|
| ION CHANNELS | | | | | | | |
| Potassium Channel, Ca2+ Act., VI | APAMIN | [125I]Apamin | 7.0E-11 | 1 or 6 | Apamin | 8.80E-11 | No |
| Potassium Channel, I[Kr] (hERG) (h) | hERG (h) | [3H]Astemizole | 1.0E-7 | 1 or 6 | Terfenadine | 2.85E-7 | No |
| Potassium Channel, I[Kr] (hERG) (h) | hERG (h) | [3H]Astemizole | 1.0E-7 | 1 or 6 | Terfenadine | 2.85E-7 | No |
| Sodium, Site 2 | BaTx | [3H]Batrachotoxin A 20-a-Benzo | 3.2E-8 | 1 or 6 | Aconitine | 8.93E-7 | No |
| Sodium, Site 2 | BaTx | [3H]Batrachotoxin A 20-a-Benzo | 3.2E-8 | 1 or 6 | Aconitine | 8.93E-7 | No |
| SECOND MESSENGERS | | | | | | | |
| Nitric Oxide, NOS (Neuronal-Binding) | NOS | [3H]NOARG | 2.5E-8 | 1 or 6 | NOARG | 2.48E-8 | No |
| Nitric Oxide, NOS (Neuronal-Binding) | NOS | [3H]NOARG | 2.5E-8 | 1 or 6 | NOARG | 2.48E-8 | No |
| PROSTAGLANDINS | | | | | | | |
| Leukotriene, LTB4 (BLT) | BLT | [3H]LTB4 | 1E-9 | 1 or 6 | LTB4 | 1.10E-9 | No |
| Leukotriene, LTB4 (BLT) | BLT | [3H]LTB4 | 1E-9 | 1 or 6 | LTB4 | 1.10E-9 | No |
| Leukotriene, LTD4 (CysLT1) | LTD4 | [3H]LTD4 | 5.0E-9 | 1 or 6 | LTD4 | 2.44E-9 | No |

FIG. 8D

| Assay | Assay Abbr. | Radioligand | Kd (M) | Test Cpd. | Reference Compound | Ki (M) Ref. Cpd. | Activity |
|---|---|---|---|---|---|---|---|
| Leukotriene, LTD4 (CysLT1) | LTD4 | [3H]LTD4 | 5.0E-9 | 1 or 6 | LTD4 | 2.44E-9 | No |
| Thromboxane A2 (h) | TXA2 (h) | [3H]SQ 29,548 | 2.0E-9 | 1 or 6 | Pinane-thromboxane | 1.74E-8 | No |
| Thromboxane A2 (h) | TXA2 (h) | [3H]SQ 29,548 | 2.0E-9 | 1 or 6 | Pinane-thromboxane | 1.74E-8 | No |
| GROWTH FACTORS/HORMONES | | | | | | | |
| Corticotropin Releasing Factor, Non-selective | CRF-NS | [125I]Tyr0-oCRF | 4.4E-9 | 1 or 6 | Tyr0-oCRF | 3.35E-9 | No |
| Corticotropin Releasing Factor, Non-selective | CRF-NS | [125I]Tyr0-oCRF | 4.4E-9 | 1 or 6 | Tyr0-oCRF | 3.35E-9 | No |
| Oxytocin | OXY | [3H]Oxytocin | 1.2E-9 | 1 or 6 | Oxytocin | 1.13E-9 | No |
| Oxytocin | OXY | [3H]Oxytocin | 1.2E-9 | 1 or 6 | Oxytocin | 1.13E-9 | No |
| Platelet Activating Factor, PAF | PAF | Hexadecyl-[3H]-acetyl-PAF | 1.7E-9 | 1 or 6 | C16-PAF | 4.19E-9 | No |
| Platelet Activating Factor, PAF | PAF | Hexadecyl-[3H]-acetyl-PAF | 1.7E-9 | 1 or 6 | C16-PAF | 4.19E-9 | No |
| Thyrotropin Releasing Hormone, TRH | TRH | [3H]-(3MeHis2)TRH | 2.3E-9 | 1 or 6 | TRH | 5.83E-8 | No |
| Thyrotropin Releasing Hormone, TRH | TRH | [3H]-(3MeHis2)TRH | 2.3E-9 | 1 or 6 | TRH | 5.83E-8 | No |
| BRAIN/GUT PEPTIDES | | | | | | | |

FIG. 8E

| Assay | Assay Abbr. | Radioligand | Kd (M) | Test Cpd. | Reference Compound | Ki (M) Ref. Cpd. | Activity |
|---|---|---|---|---|---|---|---|
| Angiotensin II, AT1 (h) | AT1 (h) | [125I]-(Sar1-Ile8) Angiotensin | 8.5E-10 | 1 or 6 | Angiotensin II | 1.81E-8 | No |
| Angiotensin II, AT1 (h) | AT1 (h) | [125I]-(Sar1-Ile8) Angiotensin | 8.5E-10 | 1 or 6 | Angiotensin II | 1.81E-8 | No |
| Angiotensin II, AT2 | AT2 | [125I]Tyr4-Angiotensin II | 4E-10 | 1 or 6 | Angiotensin II | 9.00E-10 | No |
| Angiotensin II, AT2 | AT2 | [125I]Tyr4-Angiotensin II | 4E-10 | 1 or 6 | Angiotensin II | 9.00E-10 | No |
| Bradykinin, BK2 | BK2 | [3H]Bradykinin | 4E-10 | 1 or 6 | Bradykinin TFA Salt | 3.56E-10 | No |
| Bradykinin, BK2 | BK2 | [3H]Bradykinin | 4E-10 | 1 or 6 | Bradykinin TFA Salt | 3.56E-10 | No |
| Cholecystokinin, CCK1 (CCKA) | CCK-A | [125I]CCK-8 | 3.2E-11 | 1 or 6 | CCK-8 (sulfated) | 3.44E-11 | No |
| Cholecystokinin, CCK1 (CCKA) | CCK-A | [125I]CCK-8 | 3.2E-11 | 1 or 6 | CCK-8 (sulfated) | 3.44E-11 | No |
| Cholecystokinin, CCK2 (CCKB) | CCK-B | [125I]CCK-8 | 2E-10 | 1 or 6 | CCK-8 (sulfated) | 6.98E-10 | No |
| Cholecystokinin, CCK2 (CCKB) | CCK-B | [125I]CCK-8 | 2E-10 | 1 or 6 | CCK-8 (sulfated) | 9.87E-10 | No |
| Endothelin, ET-A (h) | ETA (h) | [125I] Endothelin-1 | 1.6E-10 | 1 or 6 | Endothelin-1 | 3.01E-10 | No |
| Endothelin, ET-A (h) | ETA (h) | [125I] Endothelin-1 | 1.6E-10 | 1 or 6 | Endothelin-1 | 3.01E-10 | No |
| Endothelin, ET-B (h) | ETB (h) | [125I] Endothelin-1 | 2.1E-10 | 1 or 6 | Endothelin-1 | 1.52E-10 | No |

FIG. 8F

| Assay | Assay Abbr. | Radioligand | Kd (M) | Test Cpd. | Reference Compound | Ki (M) Ref. Cpd. | Activity |
|---|---|---|---|---|---|---|---|
| Endothelin, ET-B (h) | ETB (h) | [125I] Endothelin-1 | 2.1E-10 | 1 or 6 | Endothelin-1 | 1.52E-10 | No |
| Galanin, Non-Selective | GALNS | [I125]Galanin | 1.0E-10 | 1 or 6 | Galanin (Porcine) | 5.24E-10 | No |
| Galanin, Non-Selective | GALNS | [I125]Galanin | 1.0E-10 | 1 or 6 | Galanin (Porcine) | 5.24E-10 | No |
| Neurokinin, NK1 | NK1 | [3H]Substance P | 1.4E-9 | 1 or 6 | Substance P | 3.90E-9 | No |
| Neurokinin, NK1 | NK1 | [3H]Substance P | 1.4E-9 | 1 or 6 | Substance P | 3.90E-9 | No |
| Neurokinin, NK2 (NKA) (h) | NK2 (h) | [125I]-NKA | 5E-10 | 1 or 6 | Neurokinin A | 8.75E-10 | No |
| Neurokinin, NK2 (NKA) (h) | NK2 (h) | [125I]-NKA | 5E-10 | 1 or 6 | Neurokinin A | 8.75E-10 | No |
| Neurokinin, NK3 (NKB) | NK3 | [125I]-Eledoisin | 1.5E-9 | 1 or 6 | Eledoisin | 7.87E-9 | No |
| Neurokinin, NK3 (NKB) | NK3 | [125I]-Eledoisin | 1.5E-9 | 1 or 6 | Eledoisin | 7.87E-9 | No |
| Vasoactive Intestinal Peptide, Non-selective | VIP-NS | [125I]VIP | 1.0E-9 | 1 or 6 | VIP | 2.29E-10 | No |
| Vasoactive Intestinal Peptide, Non-selective | VIP-NS | [125I]VIP | 1.0E-9 | 1 or 6 | VIP | 2.29E-10 | No |
| Vasopressin 1 | V1 | [3H]Phenyl 3,4,5-8-Arg-Vasopr | 3E-10 | 1 or 6 | Arg8-Vasopressin | 1.81E-9 | No |
| Vasopressin 1 | V1 | [3H]Phenyl 3,4,5-8-Arg-Vasopr | 3E-10 | 1 or 6 | Arg8-Vasopressin | 1.81E-9 | No |

FIG. 8G

| Assay | Assay Abbr. | Radioligand | Kd (M) | Test Cpd. | Reference Compound | Ki (M) Ref. Cpd. | Activity |
|---|---|---|---|---|---|---|---|
| ENZYMES | | | | | | | |
| Decarboxylase, Glutamic Acid | GAD | [14C]Glutamic acid | 1.3E-6 | 1 or 6 | AminoOxy acetic acid | 7.23E-7 | No |
| Decarboxylase, Glutamic Acid | GAD | [14C]Glutamic acid | 1.3E-6 | 1 or 6 | AminoOxy acetic acid | 7.23E-7 | No |
| Esterase, Acetylcholine | ACHASE | Acetylthiocholine | 1.4E-4 | 1 or 6 | Eserine | 7.07E-7 | No |
| Esterase, Acetylcholine | ACHASE | Acetylthiocholine | 1.4E-4 | 1 or 6 | Eserine | 7.07E-7 | No |
| Oxidase, MAO-A, Peripheral | MAOA-P | [14C]-5HT (Serotonin) | 137E-6 | 1 or 6 | Ro 41-1049 | 1.32E-8 | No |
| Oxidase, MAO-A, Peripheral | MAOA-P | [14C]-5HT (Serotonin) | 137E-6 | 1 or 6 | Ro 41-1049 | 1.32E-8 | No |
| Oxidase, MAO-B, Peripheral | MAOB-P | [14C]Phenylethyl amine | 8.3E-6 | 1 or 6 | Ro 16-6491 HCl | 4.53E-8 | No |
| Oxidase, MAO-B, Peripheral | MAOB-P | [14C]Phenylethyl amine | 8.3E-6 | 1 or 6 | Ro 16-6491 HCl | 4.53E-8 | No |
| Transferase, Choline Acetyl | ChAT | [14C]Acetyl Coenzyme | 1.5E-6 | 1 or 6 | Bromoacetylcholine | 8.16E-10 | No |
| Transferase, Choline Acetyl | ChAT | [14C]Acetyl Coenzyme | 1.5E-6 | 1 or 6 | Bromoacetylcholine | 8.16E-10 | No |

ASPARTYLAMIDE INHIBITORS OF EXCITATORY AMINO ACID TRANSPORTERS

CROSS-REFERENCE TO RELATED APPLICATIONS

This application is the National Stage of International Application No. PCT/US2013/029080, filed Mar. 5, 2013, which claims the benefit of the filing date of U.S. Provisional Patent Application Ser. No. 61/606,782, filed Mar. 5, 2012, the disclosures of which are incorporated by reference in their entirety.

STATEMENT REGARDING FEDERALLY SPONSORED RESEARCH OR DEVELOPMENT

Not Applicable.

BACKGROUND OF THE INVENTION

L-Glutamate (L-Glu) is recognized as the major excitatory neurotransmitter in the mammalian central nervous system (CNS). Current estimates suggest that about 30-40% of the synapses in the mammalian CNS are glutaminergic. Glutaminergic neurons are localized in nearly all regions of the brain, with particularly high densities in the areas involved in learning and memory, such as cerebral cortex and hippocampus. In the mammalian CNS, the excitatory amino acid transporter (EAAT) family of proteins is responsible for the high-affinity sodium-dependent uptake of L-Glu into both astroglial cells and neurons. Among the five subtypes of EAAT receptors, EAAT-1 and EAAT-2 are the major contributors to L-Glu uptake from the synapse.

If L-Glu levels are not properly regulated by the EAATs and become excessive, it can result in the over-activation of excitatory amino acid (EAA) receptors and induce neuronal pathology in a process known as excitotoxicity. Rapid increases in intracellular $Ca^{2+}$ that follow the excessive activation of NMDA clas of EAA receptors can trigger both necrotic and apoptotic pathways and ultimately result in cell death. Energy consumption and increased rates of reactive oxygen species (ROS) generation are also associated with the over-activation of glutamate receptors and mitochondrial damage. Excitotoxicity is now well-recognized as a primary or secondary mechanism underlying the pathology observed in growing number of acute insults to the CNS such as ischemia, hypoglycemia, spinal cord injury and traumatic brain injury. Excitotoxicity also contributes to the development or progression of chronic neurological and neurophysiological disorders such as amyotrophic lateral sclerosis (ALS), epilepsy, schizophrenia, Huntington's disease, and Alzheimer's disease.

For example, neuronal cell death in ALS is the result of over-activation of neuronal cells due to excess extracellular L-Glu. In a normal spinal cord and brain stem, the level of extracellular L-Glu is maintained at low micromolar levels in the extracellular fluid because glial cells, which function in part to support neurons, use EAAT-2 to rapidly sequester L-Glu and restrict its access to EAA receptors. A deficiency in the normal EAAT-2 protein in patients with ALS, was identified as being important in the pathology of the disease (See, e.g., Meyer et al., *J. Neurol. Neurosurg. Psych.* 65:594-596 (1998); Aoki et al., *Ann. Neurol.* 43:645-653 (1998); and Bristol et al., *Ann Neurol.* 39:676-679 (1996)). One explanation for the reduced levels of EAAT-2 is that EAAT-2 is spliced aberrantly (Lin et al., *Neuron* 20:589-602 (1998)). The aberrant splicing produces a variant with a deletion of 45 to 107 amino acids located in the C-terminal region of the EAAT-2 protein (Meyer et al., *Neurosci. Lett.* 241:68-70 (1998)). Due to the lack of, or defectiveness of EAAT-2, extracellular L-Glu accumulates, causes neurons to be excessively activated, and includes excitotoxic pathology. Thus, the accumulation of glutamate has a toxic effect on neuronal cells because continual firing of the neurons leads to early cell death.

Small molecule agents that inhibit transport of the L-Glu by antagonizing EAATs in the CNS are considered useful molecular entities that can alter synaptic concentrations of L-Glu, can serve as in vitro and in vivo pharmacological probes of the EAATs, and in their radiolabeled forms can detect EAATs in CNS and peripheral tissues. Several EAAT inhibitors with high inhibitory potency have been described, including inhibitor variants described by Greenfield et al. (*Bioorg. Med. Chem. Lett.* 15:4985 (2005)). There remains a need, however, for EAAT antagonists that can penetrate the blood-brain barrier (BBB) to apply pharmacologically-effective concentrations to tissues and cells of the CNS.

Finally, as excitotoxic injury promoted by elevated L-Glu can result from altered regional astrocyte EAAT-2 activity or cell surface expression, EAAT antagonists that can be visualized by radiographic imaging, such as positron emission tomography (PET), are needed to allow for the quantitative assessments of these in vivo changes. The chemical synthesis and preparation of complex organic compounds for use as radiographic "tracer" compounds has proven to be unpredictable and difficult in the art (see, e.g., Lee et al., *Science* 334:639 (2011)).

SUMMARY OF THE INVENTION

In a first aspect, the invention provides compounds presented and defined by the structural Formula I

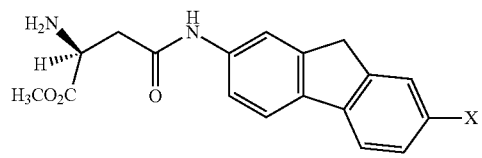

or a salt, ester or prodrug thereof, wherein
X is a halogen or radionuclide.
In one embodiment, the halogen is fluorine. In another embodiment, the halogen or radionuclide is fluorine-18. In a further embodiment, the radionuclide is carbon-11, nitrogen-13, oxygen-15, fluorine-18, zinc-62, copper-62, gallium-68, germanium-68, strontium-82, technicium-94m, iodine 124, or rubidium-82. In other embodiments, X is fluorine-18 with a specific activity of at least 1.0 Ci/mmol or 2.0 Ci/mmol. In all embodiments the compound is combined with a pharmaceutically acceptable excipient.

In a second aspect, the invention provides a method of synthesizing compound 1 presented and defined by the following structure

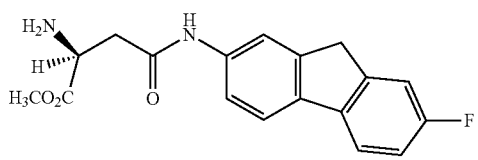

or a salt, ester or prodrug thereof, by reacting 2-amino-7-iodofluorine with bis(triaklytin) in the presence of palladium catalyst to yield 2-amino-7-triaklystannyl-fluorene, further reacting the 2-amino-7-triaklystannyl-fluorene with a N-CBz O-methylester protected L-apsartic acid fragment in the presence EDC-HCl to yield a precursor adduct, exposing the precursor adduct to fluoro-destannylation reaction such as fluorine gas or Selectafluor reagent to yield a fluorine atom appended fluorenyl ring protected product, and reacting the ring protected product with HBr to yield the compound 1.

In a third aspect, the invention provides a method of synthesizing tracer compound 2 presented and defined by the following structure

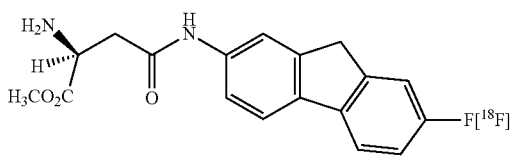

2 or a salt, ester or prodrug thereof, by reacting 2-amino-7-iodofluorine with bis(triaklytin) in the presence of palladium catalyst to yield 2-amino-7-triaklystannyl-fluorene, further reacting the 2-amino-7-triaklystannyl-fluorene with a N-CBz O-methylester protected L-apsartic acid fragment in the presence EDC-HCl to yield a precursor adduct, exposing the precursor adduct to [$^{18}$F]F$_2$ gas in liquid Freon, and reacting said ring protected product with HBr to yield the tracer compound 2.

In a fourth aspect, the invention provides a method of treating a patient suffering from or at risk of developing a neuronal disorder by administering to the patient a therapeutically effective amount of a compound presented and defined by structural Formula I

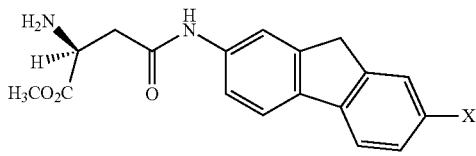

or a salt, ester or prodrug thereof,
wherein X is a halogen or radionuclide.

In one embodiment, the neuronal disorder is caused by amyotrophic lateral sclerosis, Alzheimer's disease, Huntington's disease, or ALS-parkinsonism dementia complex. In another embodiment, the neuronal disorder is caused by ischemia, hypoglycemia, spinal cord injury or traumatic brain injury. In a further embodiment, the halogen or radionuclide is fluorine or fluorine-18. In yet another embodiment, the radionuclide is carbon-11, nitrogen-13, oxygen-15, fluorine-18, zinc-62, copper-62, gallium-68, germanium-68, strontium-82, technicium-94m, iodine 124, or rubidium-82.

In a fifth aspect, the invention provides a method of detecting an excitatory amino acid transporter by contacting an excitatory amino acid transporter with a compound presented and defined by structural Formula I

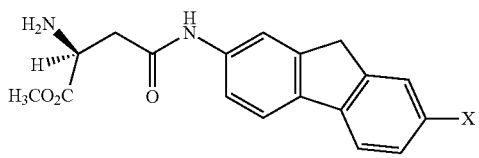

or a salt, ester or prodrug thereof,
wherein X is a radionuclide, and
detecting the compound with a radiographic scanner, such as a positron emission tomography scanner. In one embodiment, the excitatory amino acid transporter is human excitatory amino acid transporter 2. In another embodiment, the radionuclide is fluorine-18. In a further embodiment, the radionuclide is carbon-11, nitrogen-13, oxygen-15, fluorine-18, zinc-62, copper-62, gallium-68, germanium-68, strontium-82, technicium-94m, iodine 124, or rubidium-82.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

As used herein, the singular form "a," "an," and "the" include plural references unless the context clearly dictates otherwise. For example, the term "a cell" includes a plurality of cells, including mixtures thereof. The term "a nucleic acid molecule" includes a plurality of nucleic acid molecules.

As used herein, the terms below have the meanings indicated.

The term "acyl" as used herein, alone or in combination, refers to a carbonyl attached to an alkenyl, alkyl, aryl, cycloalkyl, heteroaryl, heterocyclyl, or any other moiety where the atom attached to the carbonyl is carbon. An "acetyl" group refers to a —C(O)CH$_3$ group.

An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl" as used herein, alone or in combination, refers to a straight-chain or branched-chain hydrocarbon radical having one or more double bonds optionally substituted and containing from 2 to 20, preferably 2 to 6, carbon atoms. Alkenyl refers to a carbon-carbon double on system attached at two or more positions such as ethenylene [(—CH=CH—), (—C::C—)]. Examples of alkenyl radicals include ethenyl, propenyl, 2-methylpropenyl, 1,4-butadienyl and the like.

The term "alkoxy" as used herein, alone or in combination, refers to an alkyl ether radical, optionally substituted wherein the term alkyl is as defined below. Examples of alkyl ether radicals include methoxy, ethoxy, n-propoxy, isopropoxy, n-butoxy, iso-butoxy, sec-butoxy, tert-butoxy, and the like.

The term "alkyl" as used herein, alone or in combination, refers to a straight-chain or branched-chain alkyl radical optionally substituted containing from 1 to 20 and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like.

The term "alkylamino" as used herein, alone or in combination, refers to an alkyl group optionally substituted attached to the parent molecular moiety through an amino group. Alkylamino groups may be mono- or dialkylated, forming groups such as, for example, N-methylamino, N-ethylamino, N,N-dimethylamino, N,N-ethylmethylamino and the like.

The term "alkylthio" as used herein, alone or in combination, refers to an alkyl thioether (R—S—) radical wherein the term alkyl is as defined above and wherein the sulfur may be singly or doubly oxidized. Examples of alkyl thioether radicals include methylthio, ethylthio, n-propyithio, isopropylthio, n-butylthio, iso-butylthio, sec-butylthio, tert-butylthio, methanesulfonyl, ethanesulfinyl, and the like.

The term "alkynyl" as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynyl" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like.

The term "amido" as used herein, alone or in combination, refer to an amino group as described below attached to the parent molecular moiety through a carbonyl group, or vice versa.

The term "amino" as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl" as used herein, alone or in combination, means a carbocyclic aromatic system containing one, two or three rings wherein such rings may be attached together in a pendent manner or may be fused optionally substituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 12 carbon atoms.

The terms "arylalkyl" "aralkyl" as used herein, alone or in combination, refers to an aryl group attached to the parent molecular moiety through an alkyl group.

The term "aryloxy" as used herein, alone or in combination, refers to an aryl group attached to the parent molecular moiety through an oxygen atom.

The term "polyether radical" means a polyether radical containing from 2 to 6 carbon atoms interrupted with at least one oxygen atom, such as methoxymethyl, ethoxymethyl or methoxyethoxymethyl radicals or methoxyethyl.

The terms "benzo" and "benz" as used herein, alone or in combination, refer to the divalent radical $C_6H_4=$ derived from benzene. Examples include benzothiophene and benzimidazole.

The terms "carbamate" and "carbamoyl" as used herein, alone or in combination, refers to an ester of carbamic acid (—NHCOO—) which may be attached to the parent molecular moiety from either the nitrogen or acid end, and Which may be optionally substituted as defined herein.

The term "carbonyl" as used herein, when alone includes formyl [—C(O)H] and in combination is a —C(O)— group.

The term "carboxy" as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano" as used herein, alone or in combination, refers to —CN.

The term "cycloalkyl" or, alternatively, "carbocycle", as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo-fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multicentered) saturated or partially unsaturated type. The latter type of isomer is exemplified in general by, bicyclo[1,1,1]pentane, camphor, adamantarne, and bicyclo[3,2,1 ]octane.

The term "ester" as used herein, alone or in combination, refers to a carboxy group bridging two moieties linked at carbon atoms.

The term "ether" as used herein, alone or in combination, refers to an oxygen atom bridging two moieties linked at carbon atoms.

The terms "halo" or "halogen" as used herein, alone or in combination, refers to fluorine, chlorine, bromine, or iodine.

The term "haloalkyl" as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromeihylene (—CHF—), difluoromethylene (—CF$_2$—), chloromethylene (—CHCl—) and the like.

The term "heteroalkyl" as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl" as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indobzinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocyclyl", as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocyclyl" are intended to include sulfones, suifoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocyclyl groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocyclyl groups may be optionally substituted unless specifically prohibited.

The term "hydroxyl" as used herein, alone or in combination, refers to —OH.

The phrase "in the main chain" refers to the longest contiguous or adjacent chain of carbon atoms starting at the point of attachment of a group to the compounds of this invention.

The phrase "linear chain of atoms" refers to the longest straight chain of atoms independently selected from carbon, nitrogen, oxygen and sulfur.

The term "lower" as used herein, alone or in combination, means containing from 1 to and including 6 carbon atoms.

The term "negatively-charged ion" as used herein, refers to any negatively-charged ion or molecule, either inorganic (e.g., Cl$^-$, Br$^-$, I$^-$) or organic (e.g., TsO— (i.e., tosylate)).

The term "nitro" as used herein, alone or in combination, refers to —NO$_2$.

The term "perhaloalkyl" as used herein, alone or in combination, referes to an alkyl group where all of the hydrogen atoms are replaced by halogen atoms.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstitutedsilyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Optical isomers are compounds with the same molecular formula but differ in the direction they rotate plane polarized light. There are two types of optical isomers. The first type of optical isomers are compounds that are mirror images of one another but cannot be superimposed on each other. These isomers are called "enantiomers." The second type of optical isomers are molecules that are not mirror images but each molecule rotates plane polarized light and are considered optically-active. Such molecules are called "diastereoisomers." Diastereoisomers differ not only in the way they rotate plane polarized light, but also their physical properties. The term "optical isomer" comprises more particularly the enantiomers and the diastereoisomers, in pure form or in the form of a mixture.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "imaging agent" as used herein refers to any moiety useful for the detection, tracing, or visualization of a compound of the invention when coupled thereto. Imaging agents include, e.g., an enzyme, a fluorescent label (e.g., fluorescein), a luminescent label, a bioluminescent label, a magnetic label, a metallic particle (e.g., a gold particle), a nanoparticle, an antibody or fragment thereof (e.g., a Fab, Fab', or F(ab')$_2$ molecule), and biotin. An imaging agent can be coupled to a compound of the invention by, for example, a covalent bond, ionic bond, van der Waals interaction or a hydrophobic bond. An imaging agent of the invention can be a radiolabel coupled to a compound of the invention, or a radioisotope incorporated into the chemical structure of a compound of the invention. Methods of detecting such imaging agents include, but are not limited to, positron emission tomography (PET), X-ray computed tomography (CT) and magnetic resonance imaging (MRI).

The term "neurodegenerative disorder" as used herein, refers to any disease, disorder, condition, or symptom characterized by the structural or functional loss of neurons. Neurodegenerative disorders include, e.g., Alzheimer's disease, Parkinson's disease, Huntington's Disease, Lewy Body dementia, and amyotrophic lateral sclerosis (ALS).

The phrase "therapeutically effective" is intended to qualify the amount of active ingredients used in the treatment of a disease or disorder. This amount will achieve the goal of reducing or eliminating the disease or disorder.

The term "therapeutically acceptable" refers to those compounds (or salts, esters, prodrugs, tautomers, zwitterionic forms, etc. thereof) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means mammals and non-mammals. Mammals means any member of the mammalian class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "patient" does not denote a particular age or sex.

The term "prodrug" refers to a compound that is made more active in vivo. Certain compounds of the present invention may also exist as prodrugs, as described in *Hydrolysis in Drug and Prodrug Metabolism: Chemistry, Biochemistry, and Enzymology*, Testa, Bernard and Wiley-VHCA, Zurich, Switzerland 2003. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bio-available by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug is a compound that is administered as an ester (the "prodrug"), but then is metabolically hydrolyzed to the carboxylic acid, the active entity. Additional examples include peptidyl derivatives of a compound.

The compounds of the invention can exist as therapeutically acceptable salts. The present invention includes compounds listed above in the form of salts, in particular acid addition salts. Suitable salts include those formed with both organic and inorganic acids. Such acid addition salts will normally be pharmaceutically acceptable. However, salts Of non-pharmaceutically acceptable salts may be of utility in the preparation and purification of the compound in question. Basic addition salts may also be formed and be pharmaceutically acceptable, For a more complete discussion of the preparation and selection of salts, refer to Stahl, P. Heinrich, *Pharmaceutical Salts: Properties, Selection, and Use*, Wiley-VCHA, Zurich, Switzerland (2002).

The term "therapeutically acceptable salt" as used herein, represents salts or zwitterionic forms of the compounds of the present invention which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

BRIEF DESCRIPTION OF THE DRAWINGS

FIG. 8 is a table listing central nervous system protein binding sites and binding kinetics.

DETAILED DESCRIPTION OF THE INVENTION

Figure 1:
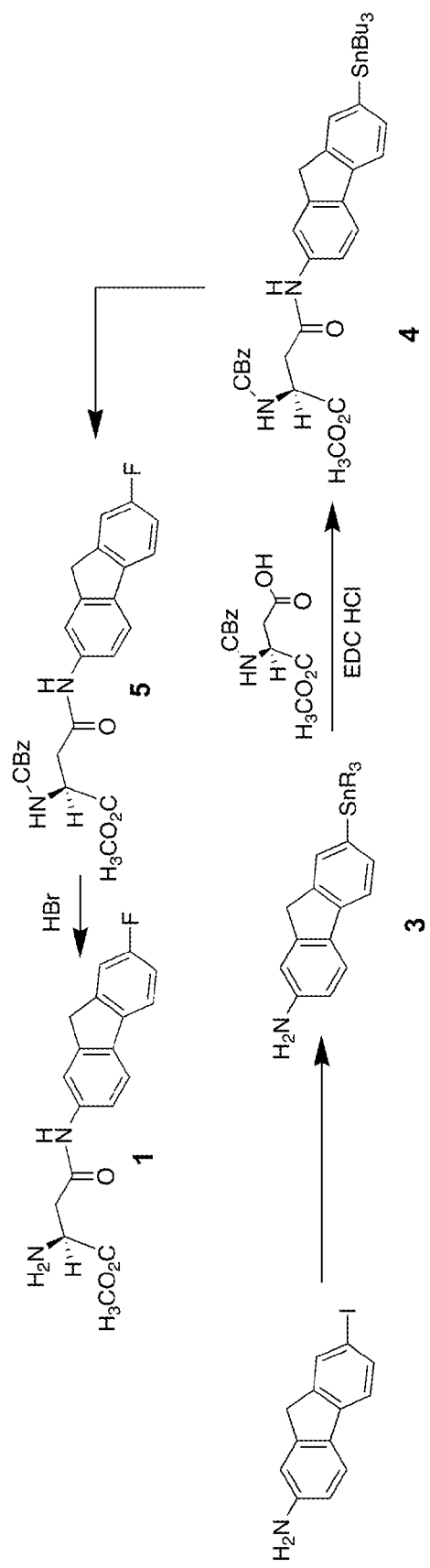
FIG. 1 is a diagram that illustrates the chemical synthesis of compound 1.

The invention features novel aspartylamide compounds that are effective inhibitors of excitatory amino acid transporters (EAATs), such as EAAT-1 and EAAT-2. The compounds of the invention are represented by the following formula:

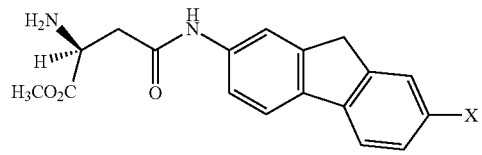

wherein X is a halogen (e.g., fluorine) or radionuclide. In one embodiment of the invention, X is a radioactive halogen, such as fluorine-18. In another embodiment of the invention, X is a radionuclide such as carbon-11, nitrogen-13, oxygen-15, fluorine-18, zinc-62, copper-62, gallium-68, germanium-68, strontium-82, technicium-94m, iodine 124, and rubidium-82. The compounds of the invention are useful for treating diseases, disorders, and symptoms characterized by or related to neuronal excitotoxicity including, but not limited to, ischemia, hypoglycemia, spinal cord injury and traumatic brain injury. The compounds of the invention are also useful for the treatment of neurodegenerative disorders such as, e.g., amyotrophic lateral sclerosis (ALS), Huntington's disease, and Parkinson's disease. Furthermore, the compounds of the invention are useful for in diagnostic imaging applications, such as the imaging of EAAT protein in the CNS by radiography, such as positron emission tomography (PET).

The compounds of the invention exhibit several qualities that represent improvements over the state of the art. First, the compounds of the invention exhibit an increased capacity to penetrate the blood-brain barrier over other EAAT inhibitors known in the art. Such increased penetrance of the blood-brain barrier allows for increased EAAT inhibition in the CNS at lower pharmacologic doses. Likewise, the increased blood-brain barrier penetration kinetics of the tracer compounds of the invention offer improved EAAT protein resolution in diagnostic imaging applications. State of the art EAAT inhibitors require an amino acid terminus on the ligand. This moiety imparts physical chemistry properties that diminish its penetration by passive diffusion across the blood-brain barrier and into the CNS. The inventors of the present invention have discovered that the addition of a methyl ester moiety to an EAAT inhibitor originally described by Greenfield et al. (variant 8; *Bioorg. Med. Chem. Lett.* 15:4985 (2005)) exhibits increased ability of the molecule to transit the blood-brain barrier without compromising EAAT inhibitory activity or specificity. This result was unexpected, as the pharmacokinetics of ester hydrolysis, in both plasma and CNS, and blood-brain barrier diffusion cannot be predicted or modeled with any certainty. Thus, in a preferred embodiment of the invention, compound 1, a lipophilic compound containing a methyl ester moiety, penetrates into the CNS and then undergoes ester hydrolysis to afford an active inhibitor of EAAT.

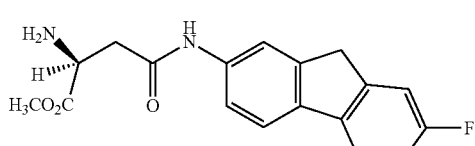

The invention further features compounds and methods useful for in vivo or in vitro radiographic imaging studies of EAAT activity in the CNS of a patient (e.g., a human). The inventors have discovered novel processes of adding a radionuclide (e.g., fluorine-18) to the methyl ester compound 1. The discovery of these compounds and related processes represent an unexpected advance in the art of radiotracer chemistry as fluorine-18 complexes are notoriously difficult to synthesize (Lee (2011)). The addition of such a radionuclide tag (e.g., fluorine-18) to the genus of EAAT inhibitors described above yields a "tracer" compound that can be imaged using, e.g., a positron emission tomography (PET) scanner. In one embodiment of the invention, compound 2 can be used to study L-Glu transporter EAAT-2 activity in the CNS (e.g., in astrocytes). Diagnostic imaging studies using these tracer compounds of the invention can be performed in vivo or in patient biopsies and tissue samples ex vivo. Similarly, the tracer compounds of the invention are also useful for the in vitro or ex vivo study of EAAT activity and neuronal excitotoxicity for biomedical research purposes.

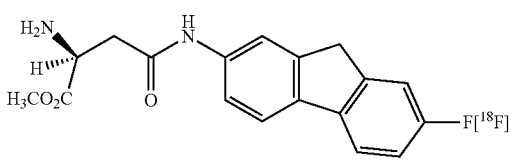

2

The invention also features methods of synthesizing the compounds of the invention described herein, as well as methods of treating a patient (e.g., a human) suffering from, or at risk of developing, a condition characterized by or related to neuronal excitotoxicity, such as a neurodegenerative disease, ischemia, stroke, or traumatic brain injury.

Neuronal Excitotoxicity

The compounds of the invention can be used as therapeutic inhibitors of EAAT activity to treat a patient (e.g., a human) at risk of developing or already suffering from neuronal excitotoxicity secondary to ischemia, hypoglycemia, spinal cord injury or traumatic brain injury. The compounds and methods of the invention may further be used to visualize EAAT transporters or proteins, such as EAAT-2, in a patient (e.g., a human) or research subject (e.g., a rodent or other animal approved for experimental use) suffering from, or at risk of developing, ischemia, spinal cord injury or traumatic brain injury.

Neurodegenerative Disorders

The compounds of the invention can be used to diagnose or treat a patient (e.g., a human) at risk of developing or already suffering from a neurodegenerative disorder, such as amyotrophic lateral sclerosis (ALS), Huntington's disease, and Parkinson's disease. The compounds and methods of the invention may further be used to visualize EAAT transporters or proteins, such as EAAT-2, in a patient (e.g., a human) or research subject (e.g., a rodent or other animal approved for experimental use) suffering from, or at risk of developing, a neurodegenerative disorder.

The compounds of the invention, when used as therapeutic inhibitors, can be used to slow or halt the progression of neurodegeneration. The compounds of the invention can also be used to diagnose neurodegeneration or follow the progression of a neurodegenerative disease when used to image EAAT protein distribution and activity in the CNS.

Methods of Prevention and Treatment

The compounds and methods of the invention can be used to treat a patient (e.g., a human) that suffers from or is at risk of suffering from a disease, disorder, condition or symptom described herein. The compounds of the invention can be used alone or in combination with other agents and compounds in methods of treating or preventing, e.g., a neurodegenerative disease (e.g., ALS) or excitotoxicity characterized by or related to ischemia, hypoglycemia, spinal cord injury or traumatic brain injury. Each such treatment described above includes the step of administering to a patient in need thereof a therapeutically effective amount of the compound of the invention described herein to delay, reduce or prevent such disease, disorder, condition, or symptom.

Besides being useful for human treatment, the compounds and formulations of the present invention are also useful for the treatment of animals, e.g., the veterinary treatment of domesticated animal, companion animals (e.g., dogs and cats), exotic animals, farm animals (e.g., ungulates, including horses, cows, sheep, goats, and pigs), and animals used in scientific research (e.g., rodents and non-human primates).

Methods of Diagnostic Imaging

Compounds of the invention that contain a radionuclide, such as fluorine-18, can also be used, alone or in combination with other agents and compounds, in radiographic medical imaging applications to diagnose or follow the progression of diseases, disorders, conditions or symptoms related to changes in EAAT expression and/or neuronal excitotoxicity (such as, e.g., a neurodegenerative disease (e.g., ALS), ischemia, hypoglycemia, spinal cord injury or traumatic brain injury) in a patient (e.g., a human). Radiologists and other medical clinicians are skilled in the use of radiographic imaging devices, such as positron emission tomography (PET) scanners, and methods of imaging tracer compounds, such as the radionuclide compounds of the invention, in a patient are widely known (e.g., Saha, Basics of PET Imaging: Physics, Chemistry, and Regulations, Springer (2010) ISBN 978-1-4419-0804-9, hereby incorporated by reference).

The radionuclide compounds and formulations of the present invention are also useful for the medical imaging of animals, e.g., the veterinary treatment of domesticated animal, companion animals (e.g., dogs and cats), exotic animals, farm animals (e.g., ungulates, including horses, cows, sheep, goats, and pigs), and animals used in scientific research (e.g., rodents and non-human primates).

Methods of Radionuclide Compound Synthesis

The radionuclide tracer compounds of the invention can be synthesized by several techniques known to persons skilled in the art. For example, for the substitution of a carbon atom by a carbon-11, several derivatives such as [$^{11}$C]methyl iodide or [$^{11}$C]methyl triflate (Welch et al., In Handbook of Radiopharmaceuticals—Radiochemistry and Applications (Welch M J, Redvanly C S Eds.), New York-Chichester-Brisbane-Toronto, Wiley-Interscience Pub., 1-848 (2003)).

In the case of a labeling with fluorine-18, the radioisotope may be directly attached to a core structure by nucleophilic aliphatic or aromatic (including heteroaromatic (Dollé et al., Curr. Pharm. Design 11:3221-3235 (2005)) substitutions or electrophilic substitutions or linked through the addition of a spacer group, both techniques known to persons skilled in the art (Kilbourn, In fluorine-18 Labeling of Radiopharmaceuticals, Nuclear Science Series (Kilbourn M R Ed.), National Academy Press, Washington, D.C., 1-149 (1990); Lasne et al., *Topics in Current Chemistry* 222:201-258 (2002); Cai et al., *Eur. J. Org. Chem.* 17:2853-2873 (2008); and Dollé et al., In Fluorine and Health: Molecular Imaging, Biomedical Materials and Pharmaceuticals, Tressaud A, Haufe G (Eds). Elsevier 3-65 (2008)). An alkyl, alkenyl or alkynyl linker may also be used for the addition of the fluorine-18 atom (Damont et al., *J. Label. Compds Radiopharm.* 51:286-292 (2008); Dollé et al., *Bioorg. Med. Chem.* 14:1115-1125 (2006); and Dollé et al., *J. Label. Compds Radiopharm.* 50:716-723 (2007)). Additional methods of producing radionuclide (e.g., fluorine-18) labeled compounds are described in U.S. Patent Application Publications No. 2006/0100465, 2010/0292478, and 2011/0184159, each hereby incorporated by reference.

In the case of a labeling with other halogens (e.g., bromine-76, iodine-123 or iodine-124), the radioisotope may also be directly attached by nucleophilic or electrophilic substitutions to a core structure or linked through the addition of a spacer group, both techniques known to persons skilled in the art (Maziere et al., *Curr. Pharm. Des.* 7:1931-1943 (2001); and Coenen et al., In Radioiodination reactions for pharmaceuticals--Compendium for effective synthesis strategies, Coenen H. H., Mertens J., Maziere B. (Eds), Springer Verlag, Berlin-Heidelberg, 1-101 (2006)).

In the case of the labeling with metal radioisotopes (e.g., gallium-68, copper-64 or technetium-99m), the preferred approach used, which will be considered by a person skilled in the art, is the use of a bifunctional chelating agent based on, for example, the open-chain polyaminocarboxylates ethylenediamine tetraacetic acid (EDTA) and diethylenetriamine pentaacetic acid (DTPA), the polyaminocarboxylic macrocycle 1,4,7,10-tetraazacyclododecane 1,4,7,10-tetraacetic acid (DOTA), mercaptoacetyldi- and triglycine (MAG2, MAG3), bis-(S-benzoyl-thioglycoloyl)diaminopropanoate ((SBT)$_2$DAP) and hydrazinonicotinic acid (HYNIC), facilitating the complexation of the radiometal cation at one function and the covalent attachment to a core molecule at another (Brunner et al., (1995) Radiotracer production—Radiometals and their chelates In Principle of Nuclear Medecine, Wagner H. N. (Ed). Saunders: Philadelphia, 220-228 (1995); Weiner R. E. et al., Chemistry of gallium and indium radiopharmaceuticals In Handbook of Radiopharmaceuticals—Radiochemistry and Applications (Welch M J, Redvanly C S Eds.), New York-Chichester-Brisbane-Toronto, Wiley-Interscience Pub., 363-400 (2003); Anderson et al., Chemistry of copper radionucleides and radiopharmaceutical products In Handbook of Radiopharmaceuticals—Radiochemistry and Applications (Welch M J, Redvanly C S Eds.), New York-Chichester-Brisbane-Toronto, Wiley-Interscience Pub., 401-422 (2003); and Mahmood et al., Technetium radiopharmaceuticals In Handbook of Radiopharmaceuticals—Radiochemistry and Applications (Welch M J, Redvanly C S Eds.), New York-Chichester-Brisbane-Toronto, Wiley-Interscience Pub., 323-362 (2003)).

Further methods of synthesizing the compounds of the invention are described below in the Examples.

Radionuclide Specific Activity

The tracer compounds of the invention described herein that include a radionuclide (e.g., fluorine-18) can be synthesized to adjust the specific activity of the compound. Specific activity is defined as the radioactivity per unit mass of a radionuclide or a labeled compound. For example, if a 50 mg sample contains 100 mCi (370MBq), then the specific activity of the sample is given as 100/50=2 mCi/mg or 74 MBq/mg. Specific activity should not be confused with the concentration of a compound containing a radionuclide, which are generally expressed in mCi/mL or MBq/mL. The specific activity is an important parameter to consider in radiolabeling and in vivo biodistribution of tracers, such as the radionuclide compounds of the invention. Cold molecules in low specific activity radiopharmaceuticals compete with radioactive molecules and lower the uptake of the tracer in the target tissue(s). Similarly, low specific activity radionuclides yield poor radiolabeling, and hence, poor radiography (e.g., PET). For these reasons, the tracer compounds of the invention containing fluorine-18 are synthesized having a specific activity of at least 1.0, 1.2, 1.4, 1.8, 2.0, 2.2, 2.4, or 2.6 Ci/mmol. In one embodiment of the invention, the fluorine-18 tracer compound has a specific activity of at least 1.0 Ci/mmol.

Persons having skill in the art are aware of methods that can increase or decrease the specific activity of a desired radionuclide compound of the invention. For example, electrophilic fluorination of palladium aryl complexes can be used to yield tracer compounds of the invention containing fluorine-18 with high specific activity (Lee et al., A Fluoride-Derived Electrophilic Late-State Fluorination Reagent for PET Imaging, *Science* 334:639 (2011), hereby incorporated by reference).

Compound Administration and Formulation

Basic addition salts can be prepared during the final isolation and purification of the compounds by reaction of a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid. The novel compounds described herein can be prepared in a form of pharmaceutically acceptable salts that will be prepared from nontoxic inorganic or organic bases including but not limited to aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally-occurring substituted amines, cyclic amines, and basic ion exchange resins, such as arginine, betaine, caffeine, choline, ethylamine, 2-diethylaminoethano, 1,2-dimethylaminoethanol, ethanolamine, ethylenediamine, N-ethyl-morpholine, N-ethylpiperidine, glucamine, glucosamine, histidine, hydroxylamine, isopropylamine, lysine, methylglucamine, morpholine, piperazine, piperidine, polyamine resins, procaine, purines, theobromine, triethylamine, trimethylamine, trishydroxylmethyl amino methane, tripropyl amine, and tromethamine.

If the compounds of the invention are basic, salts could be prepared in a form of pharmaceutically acceptable salts that will be prepared from nontoxic inorganic or organic acids including but not limited to hydrochloric, hydrobromic, phosphoric, sulfuric, tartaric, citric, acetic, fumaric, alkylsulphonic, naphthalenesulphonic, para-toluenesulphonic, camphoric acids, benzenesulfonic, benzoic, camphorsulfonic, citric, ethanesulfonic, gluconic, glutamic, isethonic, lactic, maleic, malic, mandelic, methanesulfonic, mucic, nitric, pamoic, pantothenic, phosphoric, and succinic.

While it may be possible for the compounds of the invention to be administered as the raw chemical, it is also possible to present them as a pharmaceutical formulation. Accordingly, the present invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. When used in the diagnostic imaging methods of the invention, the compounds of the invention are preferably administered to the patient (e.g., a human) by intravenous injection. The formulations may conveniently be presented in unit dosage form and may be prepared by any of the methods well known in the art of pharmacy. All methods include the step of bringing into association a compound of the present invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds of the invention may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds of the invention may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compounds of the invention may take the form of tablets, lozenges, pastilles, or gels formulated in conventional manner. Such compositions may comprise the active ingredient in a flavored basis such as sucrose and acacia or tragacanth.

The compounds of the invention may also be formulated in rectal compositions such as suppositories or retention enemas, e.g., containing conventional suppository bases such as cocoa butter, polyethylene glycol, or other glycerides.

Compounds of the invention may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include solid, liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Via the topical route, the pharmaceutical composition according to the invention may be in the form of liquid or semi liquid such as ointments, or in the form of solid such as powders. It may also be in the form of suspensions such as polymeric microspheres, or polymer patches and hydrogels allowing a controlled release. This topical composition may be in anhydrous form, in aqueous form or in the form of an emulsion. The compounds are used topically at a concentration generally of between 0.001% and 10% by weight and preferably between 0.01% and 1% by weight, relative to the total weight of the composition.

For administration by inhalation, the compounds according to the invention are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.1 to 500 mg/kg per day. The dose range for adult humans is generally from 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

Compounds according to the invention can be administered at a daily dose of about 0.001 mg/kg to 100 mg/kg of body weight, in 1 to 3 dosage intakes. Further, compounds can be used systemically, at a concentration generally of between 0.001% and 10% by weight and preferably between 0.01% and 1% by weight, relative to the weight of the composition.

The amount of active ingredient that may be combined with the carrier materials to produce a single dosage form will vary depending upon the host treated and the particular mode of administration.

The compounds of the invention can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds of the invention described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for pain involving administration of one of the compounds described herein, increased therapeutic benefit may result by also providing the patient with another therapeutic agent for pain. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of the compounds of the invention together with inert or active compounds, or other drugs including wetting agents, flavor enhancers, preserving agents, stabilizers, humidity regulators, pH regulators, osmotic pressure modifiers, emulsifiers, UV-A and UV-B screening agents, antioxidants, depigmenting agents such as hydroquinone or kojic acid, emollients, moisturizers, for instance glycerol, PEG 400, or urea, antiseborrhoeic or antiacne agents, such as S-carboxymethylcysteine, S-benzylcysteamine, salts thereof or derivatives thereof, or benzoyl peroxide, antibiotics, for instance erythromycin and tetracyclines, chemotherapeutic agent, for example, paclitaxel, antifungal agents such as ketoconazole, agents for promoting regrowth of the hair, for example, minoxidil (2,4-diamino-6-piperidinopyrimidine 3-oxide), non-steroidal anti-inflammatory agents, carotenoids, and especially p-carotene, antipsoriatic agents such as anthralin and its derivatives, eicosa-5,8,11,14-tetraynoic acid and eicosa-5,8,11-triynoic acid, and esters and amides thereof, retinoids, e.g., RAR or RXR receptor ligands, which may be natural or synthetic, corticosteroids or oestrogens, alpha-hydroxy acids and a-keto acids or derivatives thereof, such as lactic acid, malic acid, citric acid, and also the salts, amides or esters thereof, or p-hydroxy acids or derivatives thereof, such as salicylic acid and the salts, amides or esters thereof, ion-channel blockers such as potassium-channel blockers, or alternatively, more particularly for the pharmaceutical compositions, in combination with medicaments known to interfere with the immune system, anticonvulsant agents include, and are not limited to, topiramate, analogs of topiramate, carbamazepine, valproic acid, lamotrigine, gabapentin, phenytoin and the like and mixtures or pharmaceutically acceptable salts thereof A person skilled in the art will take care to select the other compound(s) to be added to these compositions such that the advantageous properties intrinsically associated with the compounds of the invention are not, or are not substantially, adversely affected by the envisaged addition.

In any case, the multiple therapeutic agents (at least one of which is a compound of the present invention) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, methods for treating diseases, disorders, conditions, or symptoms in a patient (e.g., a human or animal) in need of such treatment are presented herein, the methods comprising the step of administering to the patient an amount of a compound of the invention effective to reduce or prevent the disease, disorder, condition, or symptom, in combination with at least one additional agent for the treatment of said disorder that is known in the art.

EXAMPLES

In a related aspect, therapeutic compositions having at least one novel compound of the invention described herein can be administered in combination with one or more additional agents for the treatment of any of the diseases, disorders, conditions, or symptoms described herein.

It is understood that the foregoing examples are merely illustrative of the present invention. Certain modifications of the articles and/or methods employed may be made and still achieve the objectives of the invention. Such modifications are contemplated as within the scope of the claimed invention.

Example I

Synthesis of Compound 1

Figure 2:
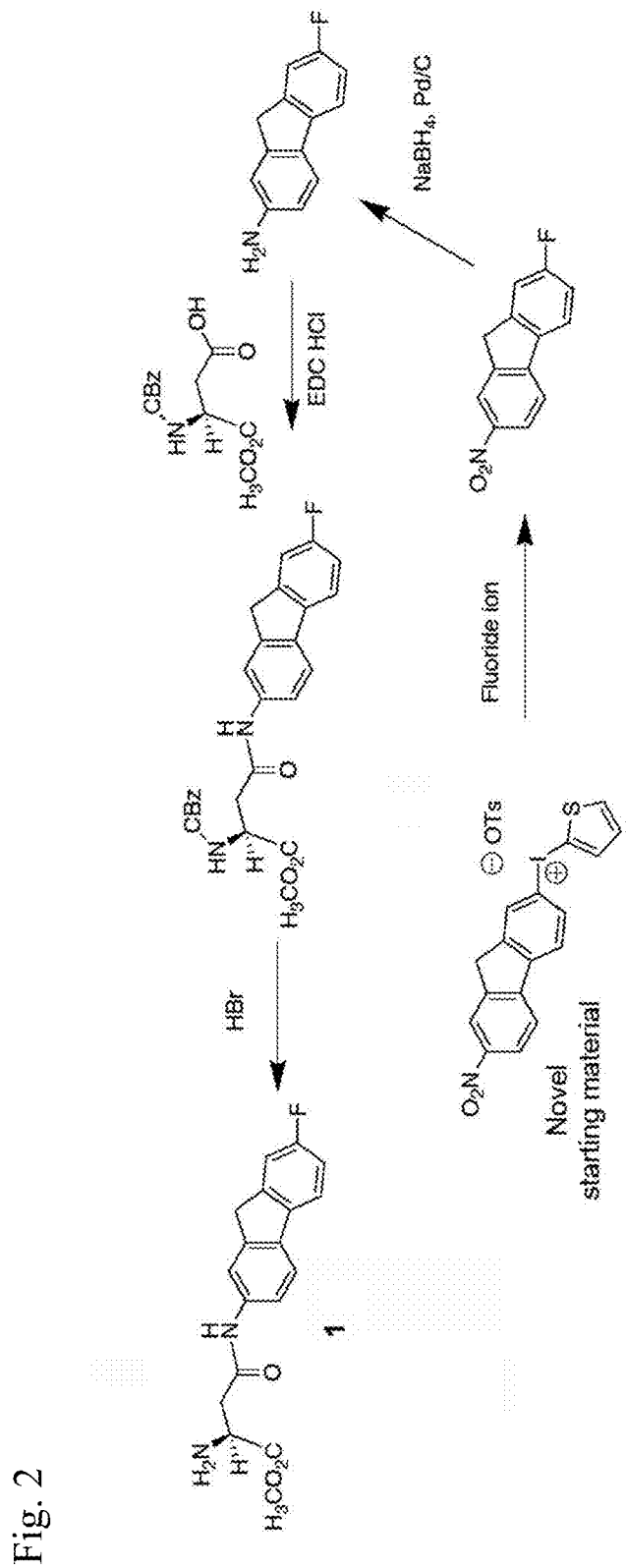
FIG. 2 is a diagram that illustrates an alternative synthesis of compound 1.

Compound 1 is prepared according to the synthetic routes shown in FIGS. 1 and 2. Each route uses a strategy of a regiospecific late-stage introduction of a fluorine atom onto a specific aromatic ring position of the fused fluorenyl ring system. A similar strategy has been used for the regiospecific introduction of a radioactive form of the fluorine atom at the same fluorenyl ring system position as described further below in the application.

FIG. 1 illustrates a third late-stage fluorine atom introduction synthesis of compound 1:

7-(Tributylstannyl)-9H-fluoren-2-amine, 3

A mixture of 7-iodo-9H-fluorene-2-amine (100 mg, 0.325 mmol), bis-tributyltin (0.32 mL, 0.65 mmol) and tetrakis (triphenylphosphine)palladium (37.55 mg, 0.032 mmol) was refluxed in dry dioxane at 100° C. for 3 h under argon. The mixture was cooled and then the volatiles were removed in vacuo. The residue was purified by preparative silica gel column chromatography (3:2, hexanes:ethyl acetate) to provide compound 3 (82.8 mg, 54%) as light brown liquid. $^1$H NMR (400 MHz, CDCl$_3$) δ7.52(d, 1H, J=7.3 Hz), 7.46-7.49 (m, 2H), 7.31 (d, 1H, J=7.3 Hz), 6.79 (s, 1H), 6.61 (dd, 1H, J=8.0, 6.0 Hz), 3.72 (s, 2H), 1.45-1.53 (m, 6H), 1.23-1.30 (m, 6H), 0.97-1.02 (m, 6H), 0.82 (t, 9H, J=7.3 Hz) ; $^{13}$C NMR (500 MHz, CDCl$_3$) 145.72, 144.98, 141.93, 137.96, 134.56, 133.19, 132.68, 120.62, 118.28, 113.92, 111.82, 36.78, 29.17, 27.45, 13.74, 9.66; LCMS (TOF ESI+) m/z 471.15, 469.42, 468.11, 467.19, 472.10, 473.11, 474.22, 475.10 (MH+, $C_{25}H_{37}$NSn; 470.27).

(S)-Methyl 2-(benzyloxycarbonylamino)-4-oxo-4-(7-(tributylstannyl)-9H-fluoren-2-ylamino)butanoate, 4

To a stirred suspension of compound 3 (50 mg, 0.106 mmol) and (3S)-4-methoxy-4-oxo-3-(phenylmethoxycarbonylamino)butanoic acid (32.76 mg, 0.116 mmol) in dichloromethane (3 mL) at room temperature was added EDC-HCl (44.66 mg, 0.233 mmol) in portions over 5 minutes. The resultant mixture was stirred at room temperature for 30 minutes, then reaction diluted with water (25 mL) and extracted with dichloromethane. The organic layer was washed with brine, dried with Na$_2$SO$_4$, and the mixture was filtered and the solvent was removed in vacuo. The resulting residue was purified by silica gel column chromatography (3:2, hexanes:ethyl acetate) to provide compound 4 (45.29 mg, 58%) as a pale yellow solid. $^1$H NMR (500 MHz, CDCl$_3$) δ7.86 (bs, 1H), 7.68 (t, 2H, J=8.3 Hz), 7.63 (bs, 1H), 7.44 (d, 2H, J=7.0 Hz), 7.30-7.35 (m, 5H), 6.06 (d, 1H, J=8.4 Hz), 5.14 (s, 2H), 4.65-4.69 (m, 1H), 3.86 (s, 2H), 3.80 (s, 3H), 3.17 (dd, 1H, J=11.7, 4.2 Hz). 2.95 (dd, 1H, J=12, 4.1 Hz), 1.53-1.59 (m, 6H), 1.33-1.37 (m, 6H), 1.01-1.15 (m, 6H), 0.90 (t, 9H, J=7.3 Hz); $^{13}$C NMR (500 MHz, CDCl$_3$) 171.43,167.88, 158.21, 144.18, 142.74,141.00,140.07, 136.13,134.65,132.92, 128.52, 128.22, 127.97, 120.06, 119.13, 118.47, 116.91, 67.09, 52.95,50.77,39.02, 36.95, 29.12, 27.41, 13.70, 9.66; HRMS m/z 735.2860, 731.2846, 733.3030, 734.3010, 736.3041, 737.2717, 739.3112 (MH+, $C_{38}H_{50}N_2O_5$Sn; 734.2742).

(S)-Methyl 2-(benzyloxycarbonylamino)-4-(7-fluoro-9H-fluoren-2-ylamino)-4-oxo-butanoate, 5

A mixture of compound 4 (7.1 mg, 0.00967 mmol) in acetone (0.5 mL) at 23° C. and ambient atmosphere was treated with silver triflate (CF$_3$SO$_3^-$Ag$^+$, 4.970 mg, 0.0193,) and 1-chloromethyl-4-fluoro-1,4-diazoniabicyclo[2.2.2]octane bis(trifluoroborate) (F-TEDA-BF$_4$, 4.08 mg, 0.0115 mmol). The reaction mixture was stirred at 23° C. for 20 minutes, then the solvent was removed. The resultant residue was treated with water (25 mL) and this mixture was extracted with chloroform. The organic solvent layer was collected, dried over $Na_2SO_4$, filtered and the solvent was evaporated in vacuo. The resultant crude pink solid was purified by silica gel column chromatography (1:1 hexanes:ethyl acetate) to afford compound 5 (2.95 mg, 66.2%) as a light pink solid. $^1$H NMR (400 MHz, $CDCl_3$) δ7.71 (bs, 1H), 7.62 (bs, 1H), 7.47-7.52 (m, 2H), 7.21-7.25 (m, 5H), 7.18 (s, 1H), 7.09 (d, 1H, J=8.8 Hz), 6.96(td, 1H, J=6.5, 2.2 Hz), 6.02 (d, 1H, J=8 Hz), 5.05 (s, 2H), 4.57-4.61 (m, 1H), 3.75 (s, 2H), 3.70 (s, 3H), 3.05 (dd, 1H, J=12.3, 3.5 Hz). 2.86 (dd, J=11.5, 4.3 Hz); $^{13}$C NMR (400 MHz, $CDCl_3$) 171.63, 168.11, 163.41, 160.98, 156.30, 145.27, 144.05, 137.52, 136.16, 135.94, 128.56, 127.98, 120.41, 119.74, 118.84, 117.02, 135.85, 112.44, 112.21, 67.16, 52.95, 50.88, 38.96, 37.00; $^{19}$F NMR (400 MHz, $CDCl_3$) 6 -116.01; HRMS m/z 463.1672 (MH+, $C_{26}H_{23}FN_2O_5$; 462.1591).

(S)-Methyl 2-amino-4-(7-fluoro-9H-fluoren-2-ylamino)-4-oxobutanoate, 1

Compound 5 (13 mg, 0.065mmol) was dissolved in a solution (3 mL) of 33% HBr in acetic acid. The mixture was stirred at room temperature for 30 minutes, and then the reaction was quenched by the addition of a saturated solution of sodium bicarbonate. The resultant mixture was extracted with ethyl acetate, the organic portion was collected and then washed with brine. The organic portion was dried with $Na_2SO_4$, filtered and the solvent was removed in vacuo. The resultant residue was purified by silica gel column chromatography (9.5:0.5, ethyl acetate:methanol) to afford compound 1 (7.91 mg, 86% yield) as a tan solid. $^1$H NMR (500 MHz, $CDCl_3$+ $CD_3OD$) δ7.76 (s, 1H), 7.65-7.60 (m, 2H), 7.44 (d, 1H, J=8.3 Hz), 7.19 (d, 1H, J=8.3 Hz), 7.02 (t, 1H, J=8.4 Hz), 4.07 (bs, 1H), 3.77 (s, 2H), 3.69 (s, 3H), 3.34 (d, 2H, J=2.25 Hz) 3.31-3.30 (m, 1H); $^{13}$C NMR (500 MHz, $CDCl_3$+ $CD_3OD$) 163.11, 161.12, 145.48, 143.55, 137.45, 136.98, 136.90, 120.11, 119.44, 118.56, 116.56, 113.48, 113.23, 111.50, 50.11, 49.12, 48.00, 36; LCMS (TOF ESI+) m/z 329.35 (MH+, $C_{18}H_{17}FN_2O_3$; 328.12).

FIG. 2 describes a second late-stage fluorine atom introduction synthesis of compound 1. Preparation of the novel 2-nitro-7-iodonium salt novel starting material was performed using synthetic transformations known within the art. Treatment of this iodonium salt starting material with fluoride ion provided 2-fluoro-7-nitrofluorine. Subsequent reduction of the nitro functional group with sodium borohydride affords the 2-amino-7-fluorofluorine product, which is then coupled to the N-CBz O-methylester protected L-apsartic acid fragment, in the presence of amide formation coupling agent EDC-HCl, to afford the cognate adduct adduct. Subsequent selective deprotection of the N-CBz carbamate protecting group of the adduct with HBr affords compound 1.

Example II

Synthesis of Compound 6

Figure 3:
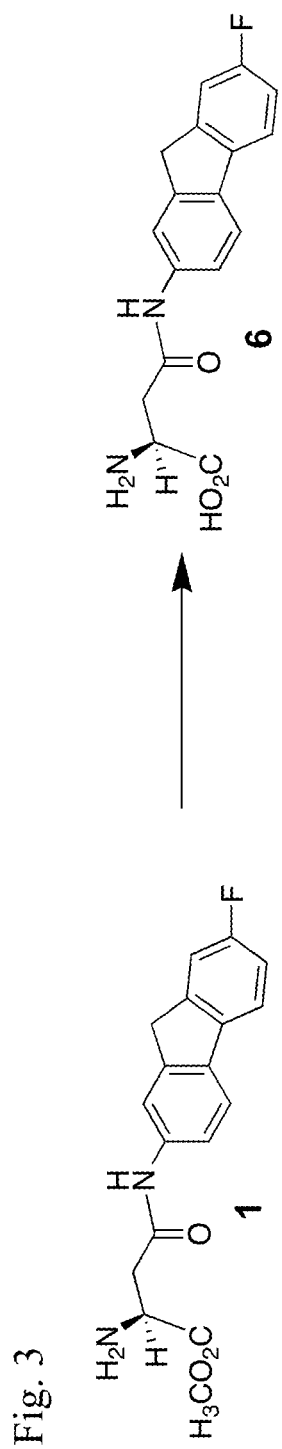
FIG. 3 is a diagram that illustrates the chemical synthesis of compound 6.

Compound 6, an EAAT2 active parent agent, is prepared using the material derived in Example I (see above), according to the synthetic route shown in FIG. 3:

(S)-2-Amino-4-(7-fluoro-9H-fluoren-2-ylamino)-4-oxo-butanoic acid, 6

Compound 1 (7.91 mg, 0.024 mmol) was dissolved in a 0° C. solution of 1:1 tetrahydrofuran:water. The mixture was stirred at 0 ° C. for 30 min, then reaction was brought to pH 7 with 1M HCl1. The resultant solution was extracted with ethyl acetate, the organic portion was collected, washed with a saturated solution of sodium carbonate then brine. The organic portion was collected, dried over $Na_2SO_4$, filtered and the solvent was removed in vacuo. The resultant residue was recrystallized using a mixture of chloroform and diethyl ether, to afford 6 (4.69 mg, 62% yield) as a tan solid. $^1$H NMR (500 MHz, $CDCl_3$+ $CD_3OD$) δ8.17 (s, 1H), 7.87 (s, 1H), 7.75-7.70 (m, 1H), 7.52 (d, 1H, J=8.3 Hz), 7.30 (d, 1H, J=8.3 Hz), 7.10 (t, 1H, J=8.4 Hz), 3.86 (s, 2H), 3.34 (d, 2H, J=2.25 Hz) 3.31-3.30 (m, 1H); $^{13}$C NMR (500 MHz, $CDCl_3$+ $CD_3OD$) 163.11, 161.12, 145.48, 143.55, 137.45, 136.98, 136.90, 120.11, 119.44, 118.56, 116.56, 113.48, 113.23, 111.50, 50.11, 49.12, 36; LCMS (TOF ESI+) m/z 315.22 (MH+, $C_{17}H_{15}FN_2O_3$; 314.10).

Example III

Compound Pharmacological EAAT2 Binding Potency

An example to demonstrate the in vitro pharmacological EAAT2 binding potency of the molecules of the invention is provided that includes compound 1 (of Example I) and compound 6 (of Example II). Separate in vitro pharmacological assays, using a method established in the literature (Esslinger et al., *Neuropharmacol.* 49:850-861 (2005)), were performed in triplicate. The excitatory amino acid transporter 2 (EAAT2) was transiently expressed in C17.2 cells using an AAV-based vector pAM-CAG-EAAT3-WPRE as described in the literature (Esslinger). Cells between passages 10-20 were seeded at $5 \times 10^4$ cells/well in 12 well plates and grown in complete DMEM supplemented with 10% fetal bovine serum, 1 mM sodium pyruvate, 0.1 mM nonessential amino acids solution. At 24 hours after plating, cells were transfected using FuGENE6 Transfection Reagent (Roche, Indianapolis, Ind.) in a ratio of 4 μL of FuGENE6 to 3 μg of purified plasmid DNA in accordance with manufacturers instructions. The cells were used in the transport assays 24 hours following transfection as described by Esslinger. Briefly, transfected C17.2 cells were grown in DMEM containing 10% FCS in a humid atmosphere of 5% $CO_2$. Near-confluent cells (plated at $5 \times 10^4$ cells/well) were rinsed with a physiological buffer (138 mM NaCl, 11 mM D-glucose, 5.3 mM KCl, 0.4 mM $KH_2PO_4$, 0.3 mM $Na_2HPO_4$, 1.1 mM $CaCl_2$, 0.7 mM $MgSO_4$, 10 mM HEPES, pH 7.4) and allowed to pre-incubate at 37° C. for 5 minutes.

Three types of binding experiments were performed: a) single concentrations of compounds 1 or 6 were added simultaneously to the cell assay with 1 μM $^3$H-D-aspartate, b) six or more concentrations of compound 6 were added simultaneously to the cell assay with 1 μM $^3$H-D-aspartate; and c) six or more concentrations of compound 6 were pre-incubated with cells for 25 minutes, after which 1 μM $^3$H-D-aspartate was added to the cell to initiate the assay. For all three binding experiment types, after a 5 minute incubation with $^3$H-D-aspartate the media was removed by rapid suction and the cells rinsed 3 times with ice-cold buffer. The cells were dissolved in 0.4 N NaOH for 24 hours and analyzed for radioactivity by liquid scintillation counting and protein by the BCA (Pierce) method. For each type of uptake assay experiment, they were conducted with at least 2 cell-containing tissue culture wells, with duplicate samples from each well analyzed for radioactivity. Each experiment were repeated a minimum of three times. Transport rates were corrected for background: i.e., radiolabel accumulation at 4° C. Initial studies confirmed that uptake quantified in this manner was linear with time and protein levels and also that uptake in un-transfected C17.2 cells was indistinguishable from background. Levels of activity were plotted as percent (%) of Control (transport in the absence of added ligands) versus the concentration of the added ligand.

In the first set of experiments, compound 6 at a concentration of 10 µM almost completely inhibited all uptake of 1 µM [$^3$H]D-aspartate uptake by EAAT2. Thus, it was advanced into the second set of experiments described below using multiple low concentrations of compound 6. In contrast, the methyl ester compound 1 exhibited little or no inhibition of 1 µM [$^3$H]D-aspartate uptake by EAAT2 at concentrations up to 10 µM. This demonstrated that under these conditions compound 1 was devoid of inhibitory ligand qualities at EAAT2. In the second set of experiments, aliquots of EAAT2 expressing cells were assayed for the uptake of [$^3$H]D-aspartate (1 µM) in the presence of six or more concentrations (10 nM to 10 µM) of compound 6. In these second assays, compound 6 and the [$^3$H]D-aspartate (1 µM) were added simultaneously and allowed to incubate with the cells for 5 minutes. Kinetic analysis was accomplished by plotting the concentration of compound 6 versus the % of Control transport (uptake in the absence of compound 6). The curve fitting software KaleidaGraph was used to estimate the concentration of compound 6. It was found that compound 6 produced 50% inhibition ($IC_{50}$) at 150 nM. In the third set of experiments, aliquots of EAAT-2 expressing cells were assayed for the uptake of [$^3$H]D-aspartate (1 µM) in the presence of six or more concentrations (10 nM to 10 µM) of compound 6. In these experiments compound 6 was allowed to incubate with the cells for 25 minutes before [$^3$H]D-aspartate was added to initiate the transport assay; where [$^3$H]D-aspartate (1 µM) was allowed to incubate with the cells for 5 minutes. Using a similar kinetic analysis as above, the resultant curve afforded an $IC_{50}$ value of 3 nM for compound 6. Thus, using the compound 6 pre-incubation time of 25 minutes in advance of treating the cells [$^3$H]D-aspartate results in enhanced potency of compound 6 at EAAT2. Therefore, the carboxylic acid compound 6 interacts very potently with EAAT2 in vitro and is considered as an EAAT2 inhibitor ligand ($IC_{50}$ value of 3 nM), whereas under the first experimental in vitro conditions employed the methyl ester compound 1 demonstrates significantly attenuated ($IC_{50}$ value >10 µM) EAAT2 interaction.

Example IV

Compound Pharmacological Selectivity for Central Nervous System Binding Sites

An example to demonstrate the pharmacological selectivity of the molecules of the invention for the central nervous system EAAT2 protein relative to other competitive binding sites within the central nervous system, is provided for compound 1 (Example I) and compound 6 (Example II). In separate in vitro competitive pharmacological assays performed in duplicate, compounds 1 and 6 at 1 micromole concentrations were evaluated against the panel of central nervous system protein binding sites that are defined in FIG. 8. As noted in FIG. 8, the assays utilized specific established radioligands for the respective competition binding assays, and respective assay ligand standards that afforded respective pharmacological inhibition binding curves of half maximal inhibitory concentration ($IC_{50}$) values. At 1 micromole assays concentrations, compounds 1 and 6 were found not to inhibit, to any observable extent, any binding of the FIG. 8 radioligands at their respective protein binding sites, as indicated by No Activity (defined as: no greater than or equal to 50% inhibition of binding). In other words, the concentrations of compounds 1 and 6 that would be required to inhibit the FIG. 8 radioligand bindings at their respective protein sites would have to be greater than 1 micromole concentration. These observations reveal that compounds 1 and 6 do not have appreciable specific in vitro binding at other CNS binding sites that have been tested.

As demonstrated in Example III, since compound 6 is found with an EAAT2 in vitro binding $IC_{50}$ value at very low nanomole concentration and at 1 micromole concentration compound 6 is found not to competitively bind to the FIG. 8 binding proteins, then it is thought that compound 6 has a selective binding profile for EAAT2 as determined by in vitro pharmacological measures. Since in vitro compound binding determinations are often indicative of in vivo central nervous system compound binding profiles, it is thought that compound 6 possesses selective EAAT2 selective binding properties in live central nervous system tissue.

Example V

Compound Brain Penetration and Metabolism in Live Mice

An example to demonstrate the ability of the brain penetration and metabolism qualities of the molecules of the invention is provided for compound 1 (of Example I) and compound 6 (of Example II). A series of separate experiments were performed with compounds 1 or 6 in groups of C57BL/6 mice (6-8 weeks old; Charles River, Wilmington, Mass.) as a function of dose and time, where concentrations of compound 6 in brain and plasma (nanogram of compound 6/g of brain tissue or blood) were measured by liquid chromatography/mass spectrometry (LC/MS-MS) detection by literature methods (Chernet et al., Life Sci. 78:340-346 (2005)). In general, doses of compounds 1 and 6 were prepared at 1, 5 or 10 mg/Kg in a homogenous solution composed of 3% dimethyl sulfoxide and 97% phosphorus buffered saline pH 7.4. Doses (0.25 mL volume) were administered by tail vein injection to groups (n≥3) of mice. Mice were sacrificed at 1, 3 10, 30, 60, 90 and 100 minutes post-injection. For some groups of mice, brains were removed, weighed, homogenized (polytron, in SDS and water) extracted with acetonitrile and then centrifuged where the acetonitrile supernatant was collected. For other groups of mice, blood was collected (≥2 mL), weighed, and then the samples were centrifuged where the supernatant plasma was collected and extracted with acetonitrile with and without 0.1% formic acid. To validate the extraction methods, other control (non-dosed) mice brains and plasma samples were spiked with various amounts (5-25,000 ng) of compound 6 and were processed in a similar fashion and then analyzed as described below. Respective acetonitrile extracts were diluted with methanol and 20 µL portions were then subjected to analytical reverse phase (C-18 analytical column, isocratic acetonitrile/water solvent) high performance liquid chromatography (HPLC), where the HPLC fractions were quantified using a mass spectrometer set to selectively monitor the mass-to-charge ratio of singly protonated compound 6 ($C_{17}H_{16}FN_2O_3$, exact mass: 315.11). In other analyses, a standard curve of compound 6 was constructed (5-25,000 nanogram mass range) and analyzed similarly. Quantities (nanograms, ng) of compound 6 from the dosed treated mouse brain and plasma samples were determined by correlation to the quantitative control spike method of detection (above) and also confirmed by interpolations against the compound 6 standard curve. Data was imported into Microsoft Excel and plotted as nanogram (ng) of detected hydrolyzed compound 1 (that is, compound 6/gram (g) brain tissue or plasma versus time (minutes). The data from the mouse experiments are shown in FIGS. 4 and 5.

Figure 4:
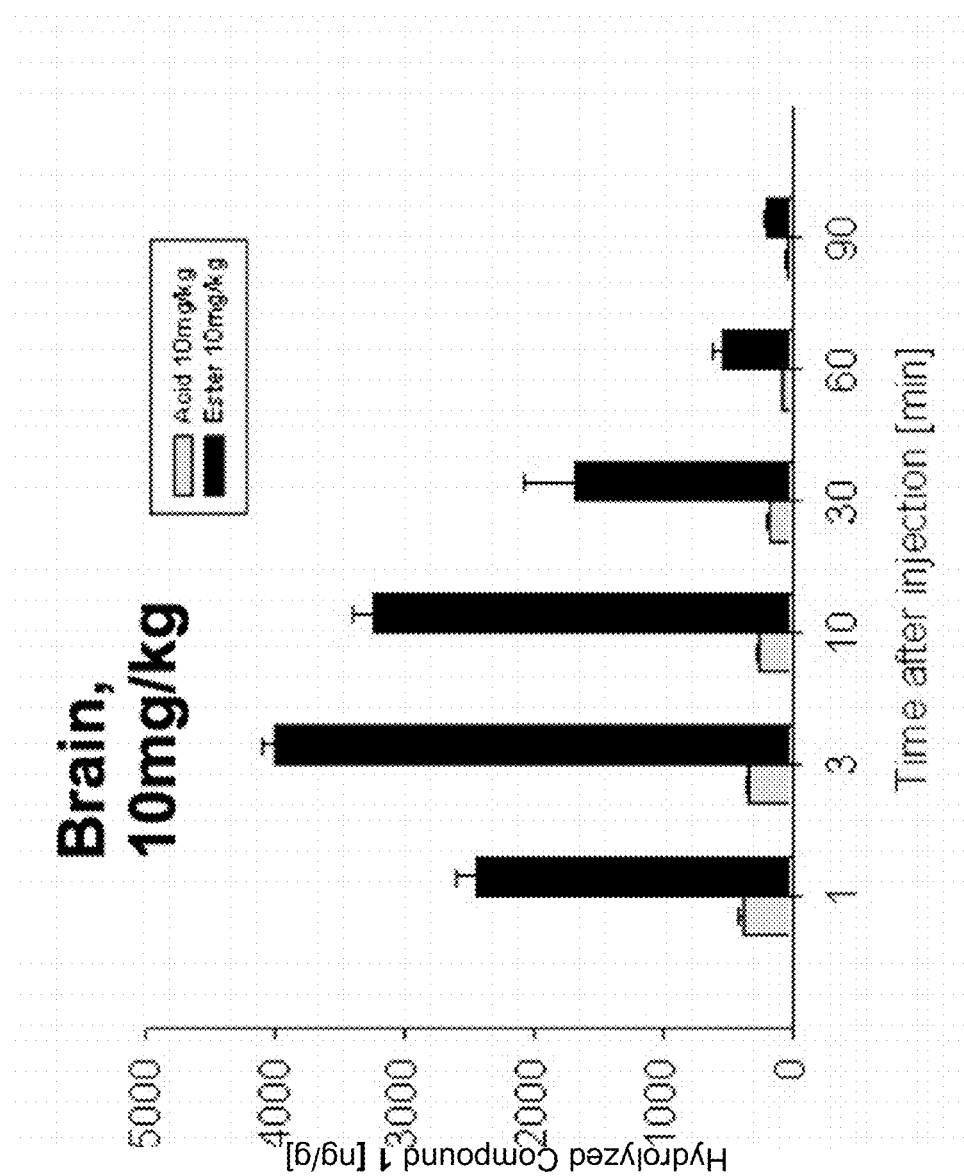
FIG. 4 is a bar graph that indicates increased diffusion of the methyl ester compound 1 ("ester"; black bars) across the blood-brain barrier versus an amino acid control ("acid"; variant 8 compound described by Greenfield et al. (*Bioorg. Med. Chem. Lett.* 15:4985 (2005)) in mouse brain following tail vein injection.

Shown in FIG. 4 are the results from 10 mg/Kg administration of the ester compound 1 (shown as black bars) or the acid compound 6 (shown as grey bars) relative to the amounts of hydrolyzed compound 1 (that is, compound 6) per gram brain tissue at time points 1, 3, 10, 60 and 90 minutes post-injection. These data reveal that at all time points higher levels of compound 6 (hydrolyzed compound 1) per gram brain tissue weight are found when compound 1 is intravenously administered, whereas lower levels of compound 6 (hydrolyzed compound 1) are detected in brain when compound 6 is intravenously administered to mice. The administered compounds each result in time dependent concentration profile detection of compound 6 (hydrolyzed compound 1). For example, when compound 1 is administered, the highest concentration of compound 6 (hydrolyzed compound 1) found in brain is at 3 minutes, with descending concentrations of compound 6 quantified thereafter to 90 minutes. Therefore, the methyl ester compound 1 has higher mouse brain penetration properties than the carboxylic acid compound 6 when administered by intravenous injection. Additionally, since the method of analysis was confirmed by spike tissue sample control determinations for compound 6, it is thought that by the intravenous administration of compound 1, that it undergoes an in vivo methyl ester hydrolysis to afford compound 6 (hydrolyzed compound 1) as found in brain. Finally, the time dependent detected quantities of compound 6 (hydrolyzed compound 1) are maximal at 3 minutes post-intravenous administration of compound 1 at 10 mg/Kg, with lesser amounts of compound 6 detected in brain thereafter.

Figure 5:
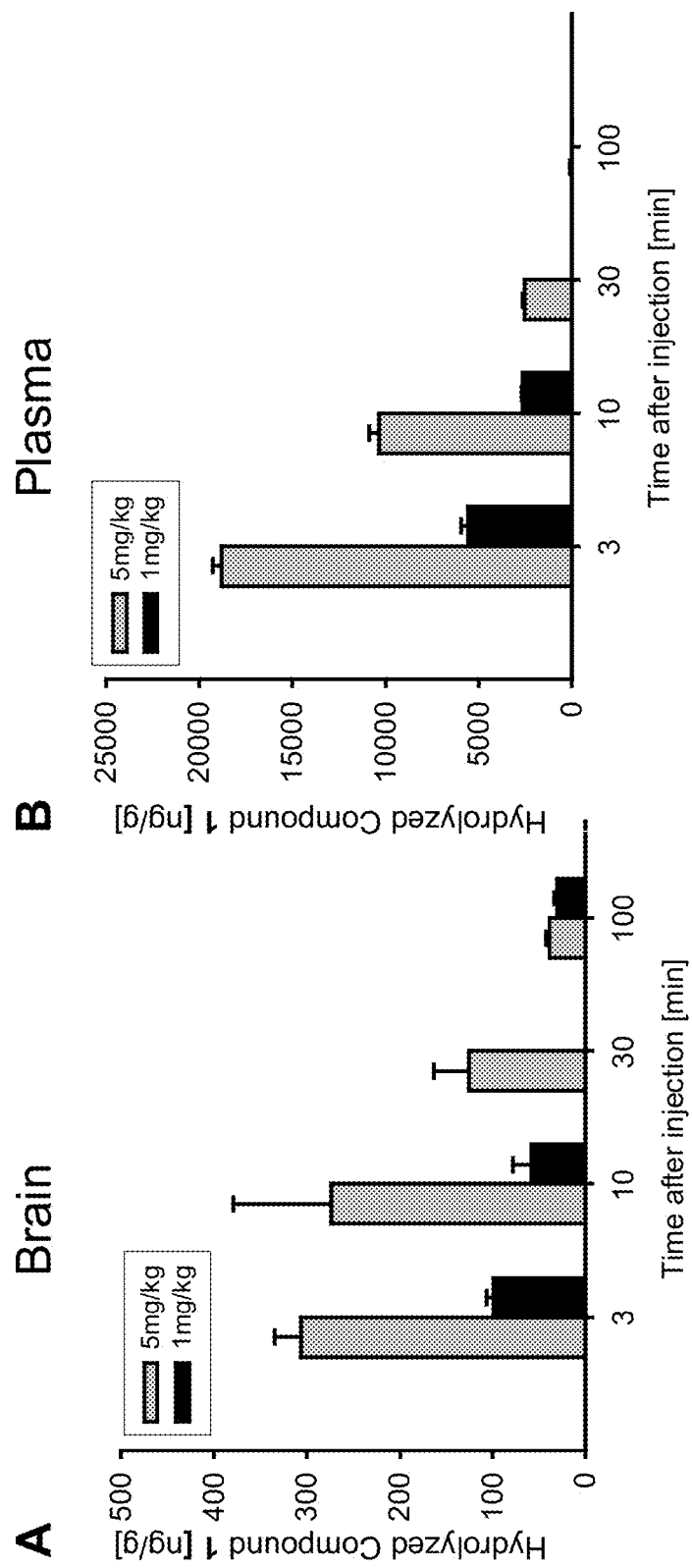
FIG. 5 are bar graphs that illustrate the dose-dependent penetration of the blood-brain barrier and subsequent hydrolysis of compound 1 in mouse brain (panel A) or plasma (panel B).

Other dose amount dependent data are shown in FIG. 5, where mice were administered the methyl ester compound 1 either at 5 mg/Kg (shown as grey bars) or 1 mg/Kg (shown as black bars), relative to the amount of compound 6 (noted as hydrolyzed compound 1) detected at 3, 10, 30 and 100 minutes post-intravenous administration. In Panel A, mouse brain tissue was evaluated, whereas in Panel B plasma samples were analyzed. In Panel A, the administration of 5 mg/kg of compound 1 resulted in higher detected levels of compound 6 in brain at 3, 10 and 100 minutes post-injection, relative to the administration of 1 mg/kg of compound 1 at those same time points. The Panel A data show a dose amount dependence with regards to the amount of compound 6 detected in mouse brain as a function of time. Furthermore, the Panel A data for the 5 mg/Kg dose of compound 1 determined at 3, 10, 30 and 100 minutes post-injection reveal the highest concentration of detected compound 6 (noted as hydrolyzed compound 1) at the early 3 and 10 minute times, with descending lower levels of compound 6 measured at the times of 30 and 100 minutes post-injection of compound 1. In Panel B, the 5 mg/Kg administration of compound 1 results in higher detected quantities of compound 6 (noted as hydrolyzed compound 1) in plasma at 3 and 10 minutes post-injection, relative to the administration of 1 mg/Kg of compound 1 at the respective 3 and 10 minute time points. The Panel B plasma sample data show a dose amount dependence for the amount of compound 6 detected in plasma at 3 and 10 minutes post-injection of compound 1. Additionally, the Panel B data for the 5 mg/Kg dose of compound 1 determined at 3, 10 and 30 minutes post-injection reveal the highest concentration of detected compound 6 at the early 3 minute time, with descending lower levels of compound 6 found at the times of 10 and 30 minutes post-injection of compound 1.

The data presented in FIGS. 4 and 5 provide evidence that after intravenous injection of compound 1, compound 1 enters mouse brain, where compound 1 is thought to undergo an in vivo hydrolysis to compound 6 (hydrolyzed compound 1), and that detected quantities of compound 6 in brain tissue and plasma samples over 0-90 minutes post-injection are considered a function of the compound 1 intravenous dose amount given.

Example VI

Fluorine-18 Tracer Radioynthesis (Compound 2)

Figure 6:
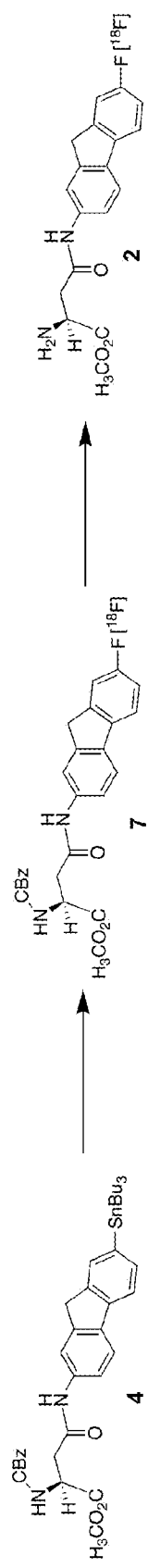
FIG. 6 is diagram that illustrates the chemical synthesis of compound 2, a tracer compound of the invention.

FIG. 6 illustrates the radiochemical synthesis of the EAAT2 positron emission tomography (PET) imaging tracer compound 2, in which the radiosynthesis is patterned after the last 2 synthetic steps detailed in Example I (above). Accordingly, FIG. 6 serves as an example for fluorine-18 ($[^{18}F]$) radiolabeling reactions to afford tracer compound 2 of the invention.

$[^{18}F]$Fluorine gas ($[^{18}F]F_2$) was produced with a Siemens RDS Eclipse cyclotron (Knoxville, Tenn.) using methods described by others (Hess et al., *App. Radiat. Isotopes* 57:185-191 (2002)). Freon-11 ($Cl_3CF$), 33% hydrobromic acid in acetic acid (HBr, $CH_3CO_2H$), methanol, acetonitrile, and trifluoroacetic acid were reagent grade or better, used without any additional purification, and were purchased from Aldrich Chemical Company (Milwaukie, Wis., USA). USP grade propylene glycol, polyoxyl-35 castor oil, ethanol, and phosphate buffered saline pH 7.4 were also purchased from Aldrich Chemical Company. The Sep-Pak® Plus C18 cartridges (Waters, Milford, Mass.), were used for solid phase extractions (SPE).

A 12 mg portion of compound 4 (per Example I) was placed in a 6 mL Pyrex tube charged with a magnetic stir bar, and then 4 mL of Freon-11 was added. The mixture was stirred for a short period at room temperature to provide a homogenous solution. The Pyrex reaction tube was fitted with a rubber septum, and through the septum was placed a short needle extending into the non-liquid head-space of the Pryrex tube. External to the septum, the short needle was fitted with a length of tubing that was joined to a soda lime trap to capture any exhaust gasses. A second needle was placed through the septum, where this needle extended into the Pyrex reaction vessel to the distance where the needle tip was in contact with the Freon-11 solution. A stream of $[^{18}F]F_2$ gas from the cyclotron, mixed with argon gas, was bubbled slowly into Freon-11 solution for a period of 6-7 minutes. Thereafter the $[^{18}F]F_2$ $_{gas}$ delivery needle was removed from the Pyrex reaction vessel. A third needle was inserted through the septum and into the Pyrex reaction vessel to a distance just above the Freon-11 solution to deliver a stream of helium gas. Helium gas was passed over the solution until all of the Freon-11 liquid was removed leaving a brown residue. The residue was treated with 700 µL of 33% hydrobromic acid in acetic acid. The mixture was stirred at room temperature for 1.5 hours. Thereafter, the reaction mixture was treated with 2 mL of a solution of 1:3 methanol:distilled water, and then 650 µL of 10.8 M sodium hydroxide to bring the solution mixture to pH 5. This acidified mixture was taken up onto C18 Plus Sep-Pak® that had been conditioned beforehand with methanol followed by distilled water. The C18 Plus Sep-Pak® was flushed with distilled water (6 mL) and then flushed with seven methanol 200 μL portions. The first three methanol cartridge eluted portions were combined to provide a composite solution for high performance liquid chromatographic (HPLC) purification.

Semi-preparative HPLC was performed on the composite methanol solution containing tracer 2, using a GP50 HPLC system (Dionex, Sunnyvale, Calif.) UV (254 nm) and radioactivity detectors, with a 10 mm×250 mm Luna C-18 column (Phenomenex, Torrance, Calif.). The column was eluted with an isocratic solvent mixture of 0.1% trifluoroacetic acid (aq) and the balance as 1:1 methanol:distilled water. The major radioactive peak containing tracer 2 was collected. The average decay corrected radiochemical yield of tracer 2 was ~3.5% (n=5).

The HPLC collected tracer 2 was diluted with 35 mL of distilled water and then taken up onto C18 Plus Sep-Pak® cartridge that had been conditioned beforehand with acetonitrile followed by distilled water. The C18 Plus Sep-Pak® cartridge was flushed with distilled water (10 mL) and then flushed with seven acetonitrile 200 μL portions. The first three acetonitrile cartridge eluted portions were combined in a glass tube, which was then subjected to a moderate stream of nitrogen gas to remove the acetonitrile solvent. The residue remaining in the glass tube was formulated into an injection dose by diluting the residue with 150 μL of propylene glycol, 50 μL polyoxyl-35 castor oil, 12.5 μL of ethanol, and ~238 μL of phosphate buffered saline pH 7.4. Larger or smaller dose volumes of the same four component formulation in their respective relative proportions are also suitable for injection. The radiosynthesis, purification, and dose formulation time was ~2.5 h (n=5).

Analytical HPLC was performed with a Breeze HPLC system (Waters, Milford, Mass.) with a 4.6×250 mm Luna C-18 column (Phenomenex, Torrance, Calif.), with an isocratic elution solvent mixture of 0.1% trifluoroacetic acid (aq) and the balance as 1:1 methanol:distilled water. Analytical HPLC was performed on small aliquots (2 μL) of formulated tracer 2 detected by radioactivity and UV (254 nm). Analytical HPLC demonstrated co-elution retention times of tracer 2 and the compound 1 standard. Radiochemical purity of the tracer 2 formulated dose was found to be >95%. To determine specific activity, a standard curve was constructed using the areas under the analytical HPLC 254 nm peak of compound 1 standard (for example, 0.000327 μmol and 0.00383 μmol). Formulated radiopharmaceutical tracer 2 aliquots were evaluated by analytical HPLC. The areas under the peak for tracer 2 were interpolated against the standard curve to determine the mass of compound 1, from which specific activity was calculated. The average specific activity of tracer 2 at the time of injection was calculated as 2.4 Ci/mmol (n=5).

Example VII

Tracer Brain Imaging and Quantitative EAAT2 Detection in Rodent Subjects

As an example of the tracer compound of the invention, rodent (rat) quantitative in vivo PET imaging trials are presented employing the tracer compound 2 of Example VI. The in vivo PET imaging was performed in parallel with magnetic resonance (MR) and computed axial tomography (CAT, CT) imaging methods, in which the latter two imaging methods afforded anatomical tissue information for co-registration to the acquired tracer quantitative PET data. The co-registration of imaging data sets allows for the definitions of tissue regions of interest (ROIs) that possess various EAAT2 tissue densities (concentrations). Two rodent imaging trials (A-B) were performed employing two age-matched male Sprague-Dawley subjects. The age of the subjects were nearly identical to those described in the most recent rat (Sprague-Dawley, amongst others) stereotaxic brain atlas (Paxinos et al., "The Rhesus Monkey Brain in Stereotaxic Coordinates," Academic Press: Burlington, Mass. (2007)) providing high confidence levels for identification and definition of explicit brain cerebral fine tissue structures as regions of interest (ROIs) for quantitative analysis, and as a function of three-dimensional (3D) co-registration of cerebral soft tissue identification by MR scan analysis and landmark anatomical features from CAT data. Details of the two subject (A and B) imaging tracer trial are summarized in Table 1.

TABLE 1

| Trial | Rat Subject Age (days) | Rat Subject Weight (g) | Tracer Specific Activity (Ci/mmol) | Tracer Dose (mCi) | Tracer Dose Volume (mL) | Compound 1 Pre-administration (6 mg/Kg dose) | Challenge dose volume (mL) |
|---|---|---|---|---|---|---|---|
| A | 91 | 371 | 2.4 | 0.490 | 0.46 | None | None |
| B | 91 | 371 | 2.4 | 0.487 | 0.44 | 2.22 mg | 0.45 |

The PET data were acquired with a Siemens Inveon microPET scanner (ca. 1.5 mm spatial resolution). Rodent subject tail vein tracer 2 injection volumes (Table 1) used the tracer 2 dose formulation described in Example VI. Tail vein injections of the tracer in the dose formulation were followed by a 0.3 mL saline flush. The challenge (blocking) Trial B was accomplished by injection of the non-radioactive form of the tracer, e.g., compound 1 as described in Example II, (6 mg/kg dose) in 0.45 mL of a similar dose formulation as was used for the tracer. The trial B challenge dose was given by tail vein injection 10 minutes prior to administration of tracer 2. PET imaging was performed within a northermic (35° C.) multi-modal rodent imaging chamber with the rat under anesthesia (isoflurane 1-1.5%). The dynamic microPET data were acquired over 90 minutes beginning at the time of injection of tracer 2. The PET data were reconstructed as 18 frames, 300 seconds per frame. Magnetic resonance (MR) data were acquired with a Bruker Biospin 7-Tesla magnet multi-slice 2D FLASH (T2*-weighted gradient recall echo, TR =1528.3 msec, TE=7 msec, 256×256×50 voxels, 16 μm³ resolution). Computed axial tomography (CAT) data were acquired with a Siemens MicroCAT II scanner in standard rat mode (80 kVp, 225 mA; 400 ms exposure, 194 steps×194 degrees, 97 micron isotropic resolution).

MR, microCAT and microPET files were processed with AMIDE open source software (Loening et al., *Molecular Imaging* 2:131-137 (2003)), version 0.9.0. (and also later versions). MR and CT images were oriented as defined by Paxinos. Cranial landmarks of bregma and lambda were identified from the CT images. The X, Y, Z coordinates of imaging views were centered as bregma=origin of trial A. Consistent landmark structures were iteratively co-registered and template fit against the cranial structures of the trial A landmarks, and cross checked against cerebral soft tissues observed from the MR scan data. All PET scan data were decay time corrected, quantified with a phantom instrument calibration factor, and regional central nervous system radioactivity is reported as Standardized Uptake Value (SUV) defined as: (MBq in the tissue region of interest/ decay corrected injected dose at time=0) / body weight of the rat as Kg (Innis et al., *J. Cereb. Blood Flow Metab.* 27:1533-1539 (2007)).

Each PET data set was iteratively co-registered to respective CT skull data and fine adjustments were made using the trial A microPET data as a template. Central nervous system tissue regions of interest (ROIs) were defined conservatively (well within the ROI volume size limits and locations) against their stereotaxic 3D locations (Paxinos) and correlated with the MR tissue landmarks. The central nervous tissue ROIs are defined as follows: HC as hippocampus, FrCTX as frontal cortex, CP as caudate-putamen, TH as thalamus, CE as cerebellum, HB as hind brain, MotCtx as motor cortex, and Lumbar as lumbar spinal region. ROI PET scan statistics were exported to Excel and the graph of FIG. 7 was generated using GraphPad Prism software.

Based upon the determinations of Example III where compound 6 binds to EAAT2 and compound 1 possesses significantly less EAAT2 binding potency; and also from Example V, where intravenous tail vein administration of compound 1 results in the detection of compound 6 in rodent brain over the pharmacokinetic time course of 0-90 minutes, then when tracer 2 is administered by the same intravenous tail vein route into rat it is thought that a metabolite form of tracer 2, similar to non-radioactive carboxylic acid compound 6, is produced in vivo. This in vivo metabolite form of tracer 2 is considered as the fluorine-18 labeled form of compound 6, and it is thought that this metabolite interacts with the EAAT2 target protein in rodent brain. Known ROI EAAT2 rodent brain distribution densities determined by immunohistochemical and related methods carried out by others (Rothstein et al., *Neuron* 13:713-725 (1994); Berger et al., *Ant. Embryol.* 198:13-30 (1998); Lehre et al., *J. Neurosci.* 15:1835-1853 (1995); Lehre et al., *J. Neurosci.* 18:8751-8757 (1998); and Danbolt, *Prog. Neurobiol.* 65:1-105 (2001)) were used to compare to the relative cerebral ROI EAAT2 interactions of tracer 2 and its cognate metabolite. Therefore, the relative comparisons of EAAT2 detection SUV signals found within the brain ROIs are particularly meaningful when extrapolated to the known rodent EAAT2 tissue distributions detected by other non-PET scanning means (Rothstein, Berger, Lehre 1995, Lehre 1998, and Danbolt). The performance of tracer 2 and its metabolite alone (baseline scan, unblocked) and challenged (in the presence of compound 1, 5.0 mg/Kg; EAAT2 challenge, blocked)) in key central nervous system regions of interest over time is shown graphically in FIG. 7.

Figure 7:
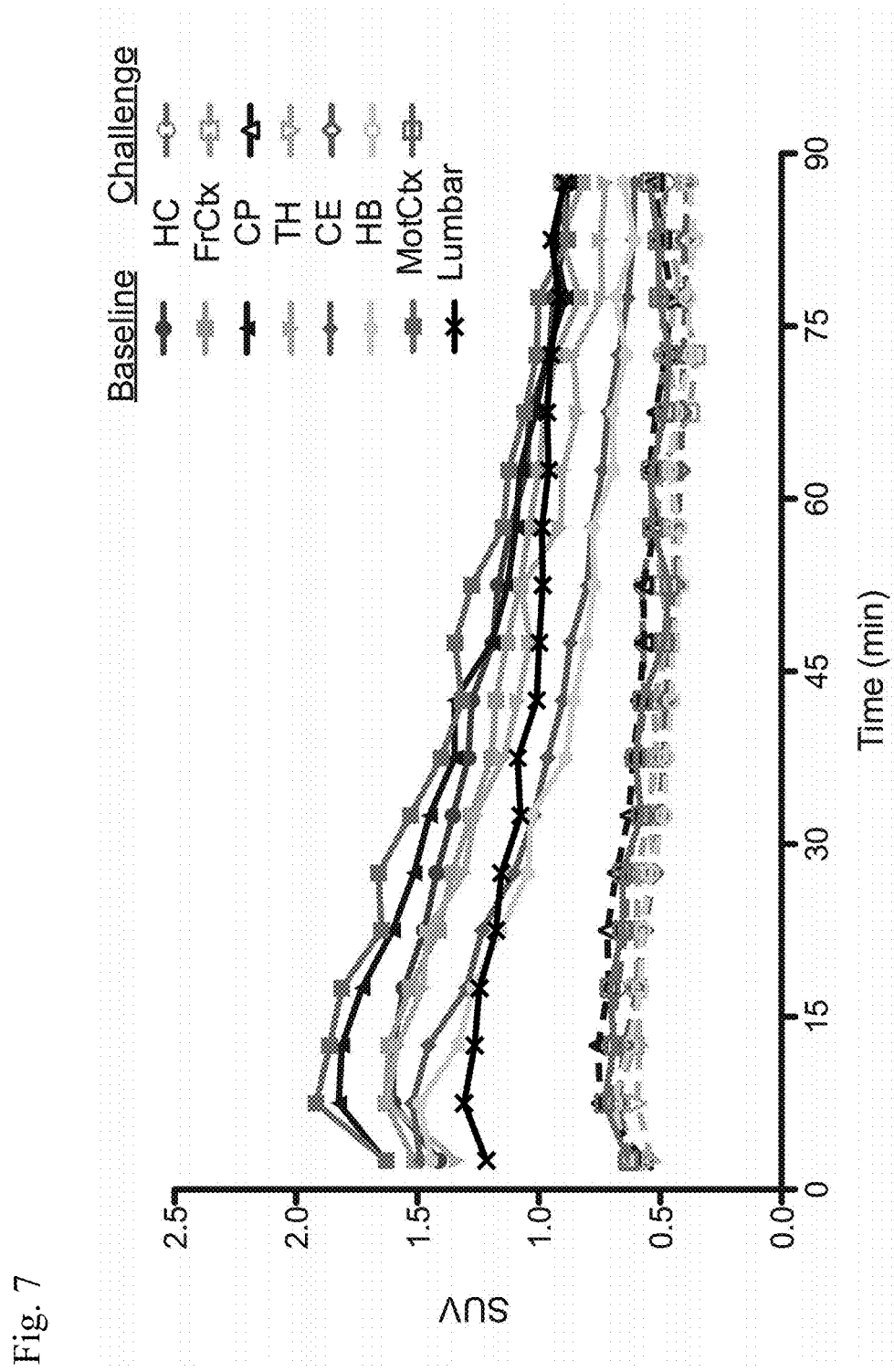
FIG. 7 is line graph that illustrates tracer brain imaging and quantitative EAAT2 detection in rodent subjects. The central nervous tissue ROIs are defined as follows: HC as hippocampus, FrCTX as frontal cortex, CP as caudate-putamen, TH as thalamus, CE as cerebellum, HB as hind brain, MotCtx as motor cortex, and Lumbar as lumbar spinal region.

The tracer time-activity curves of FIG. 7 (upper panel, solid lines) show the injected tracer 2 penetrates brain, and at various times post-injection, discrete radioactivity SUV signals per tissue ROI are observed over the course of 0-90 minutes post-tracer injection. The PET tracer 2, and its metabolite, affords tissue radioactivity pharmacokinetic curves that are observed with uptake, maximum and wash-out phases over the course of 90 minutes post-tracer 2 injection. The PET scan determined FIG. 7 brain radioactivity time courses resemble the time courses observed with the non-radioactive determinations using compound 1 described in Example V. The EAAT2 density rich hippocampus, caudate-putamen, and motor cortex regions are with the high tracer 2 and its metabolite radioactivity SUV signals (approximately 10 minutes post-tracer 2 injection and beyond to 90 minutes) that are indicative of EAAT2 interactions. Frontal cortex, thalamus, and lumbar spine regions are with moderate tissue SUV signals. The cerebellum and hind-brain regions are with lower tracer 2 and its metabolite regional tissue SUV signals. All of these observations are consistent with other relative central nervous system tissue EAAT2 density determinations (Rothstein, Berger, Lehre 1995, Lehre 1998, and Danbolt). Therefore, EAAT2 is detected quantitatively in discrete central nervous system tissue ROIs with various known EAAT2 distributions across live rat brain after tracer 2 is administered by intravenous injection.

The FIG. 7 challenge study with compound 1 (5 mg/Kg dose, hatched lines within FIG. 7) reveals a significant reduction of SUV radioactivity signals across all central nervous tissue ROIs. For example, pre-administration of the compound 1 significantly reduces (2-3 fold) tissue SUV signals at all times post-tracer 2 injection. These observations support the conclusion that interactions tracer 2 and its metabolite at EAAT2 are attenuated in the presence of compound 1. Additionally, these observations provide evidence that tracer 2 and its metabolite are interacting with EAAT2 in a specific way; for example, as shown in the absence of a compound 1 challenge dose, and per the baseline (unblocked, unchallenged) SUV pharmacokinetic tissue activity radioactivity profiles of FIG. 7. Since rat EAAT2 central nervous system distributions have been correlated to EAAT2 distributions in primate brain (Danbolt) and given that tracer 2 and its metabolite detect EAAT2 in rat brain, then tracer 2 and its metabolite are thought capable of detecting EAAT2 in the central nervous tissues of primate brain. It is established that central nervous system transporter targeted PET imaging outcomes found in rodents are often similar in non-human primates and also humans (Huang et al., *Curr. Topics Med. Chem.* 10:1499-1526 (2010)).

Example XIII

Tracer Brain Imaging and EAAT2 Detection in Primate Subject

Another example of the invention includes the in vivo detection of EAAT2 in live primate brain. For example, the PET imaging tracer 2 of Example VI was evaluated in male Rhesus monkey (*Macaca mulatta*, male, 5.06 Kg, 3 years and 2 months old) using PET correlated to magnetic resonance (MR) imaging scans across brain tissue. The PET imaging scans allowed the detection of EAAT2 within cerebral tissue regions of interest (ROIs). The MR scans were used to identify soft tissue ROIs that that allowed the co-registration of the PET scan three-dimensional (3D) brain tissue EAAT2 tracer radioactivity data. Typical brain scan methods are as follows.

The imaging primate subject (nor-thermic, 35° C.) was placed under anesthesia (1-1.5% isoflurane ventilation). MR scan data were acquired with a GE Signa LX (Milwaukee, Wis.) 1.5-Tesla magnet and quadrature head coil. A 3-axis MR scout scan was initially run to determine localization coordinates. The subject was positioned within the MR scanner head first in sternal recumbancy. MR cerebral scan images were acquired using a T1-weighted 3D SPGR sequence with the following parameters: TR=22 msec, TE=7.9 msec, FA=30 degrees, RBw=15.63 kHz, 4 averages, 256×256 matrix, 84×1 mm slices, 16 cm field of view, and 625 µm in-plane resolution). A fiducial marker (vitamin E filled) on the left side of the subject's head was used to mark the MR scan head orientation for subsequent MR-PET scan co-registrations.

The PET scan data were acquired with a Siemens Micro-PET P4 Focus scanner that is characterized with ca. 1.8 mm$^3$ spatial resolution at center of the field of view (Tai et al., *Phys. Med. Biol.* 46:1845-62 (2001)). Administration of tracer 2 was by bolus injection via the intravenous saphenous catheter. The tracer dose was a 1.9 mL injection volume, as a solution as per four component dose formulation composition described in Example VI. The dose contained 2.33 mCi of tracer 2 with a determined specific activity of 2.82 Ci/mmol. PET scan data were sampled over a 5 h period post injection of tracer 2. The data were reconstructed with a maximum a priori (MAP) protocol with output as Concorde/microPET image files. The scan data reconstruction parameters were as follows: 0.8 mm in-plane resolution, smoothing parameter of 0.1, MAPTR attenuation/scatter correction, and as either a single frame or multiple frames.

The MR and PET scan files were processed and co-registered with AMIDE open source software (Loening). The co-registration of MR and PET data sets were as follows. The centers of the cerebral tissues of the anterior and posterior commissures were identified and used as key 3D brain tissue landmarks. MR images were oriented to place the vitamin E fiducial mark consistent with the axes in AMIDE and as per Paxinos and also the BrainInfo *Macaca fascicularis* line drawings/sectional slices of the online atlas http://braininfo.rprc.washington.edu and the BrainMaps.org *Mucaca mulatta* sectional slice online atlas http://brainmaps.org. Using these atlases, the respective views and the tissue landmarks therein, the subject brain tissues were oriented in a sagittal perspective facing left, anterior and posterior commissure marks in the same horizontal plane, and the coronal and transverse views symmetrical about the brain medial line.

The x, y, and z 3D coordinate origin was defined for the cerebral views as the center of the anterior commissure; as per the online atlases of the http://braininfo.rprc.washington.edu and http://brainmaps.org. The single frame reconstructed PET data was iteratively co-registered to the MR data. For example, MR soft tissue landmarks were correlated with the PET scan landmarks (including: eyes, jaw-line, connective tissue, amongst others) affording discrete co-registered planes of recognized views. After co-registration, a transformation matrix that defined a center and rotational coordinates from the single frame PET data were made to obtain an identical co-registration as per the single frame data.

Whole brain and the cerebral ROIs were drawn conservatively against their stereotaxic 3D locations (Paxinos), and also http://braininfo.rprc.washington.edu and http://brainmaps.org). PET brain data were analyzed as whole brain, which included cerebral locations that were defined (ROI x, y, z millimeters from anterior commissure). The cerebral ROIs were defined as thalamus (primarily, dorsolateral thalamic nuclei), frontal cortices (including, somatosens and motor cortices), the hippocampus, amongst other regions. The PET data were decay and time corrected. The corrected scan data were transformed to Standardized Uptake Value (SUV) defined as: (MBq in the tissue region of interest/ decay corrected injected dose at time=0)/body weight of the monkey as Kg (Innis) subsequently exported to Microsoft Excel.

The evaluation of whole brain penetration and regional distribution of tracer 2 revealed maximal whole brain 2.42 SUV tracer activity within one hour after injection of 2. Over the course of 5 hours, brain tissue underwent loss of tracer 2 activity. For example, the pharmacokinetic profile at four hours post tracer 2 injection revealed whole brain radioactivity had decreased from 2.42 SUV at the one hour time to 0.29 SUV at four hours. High levels of tracer 2 activities were found in the thalamus, frontal cortices and hippocampal regions between 0 and 2 hours post tracer 2 injection. Thus, whole brain and regional brain tissue tracer radioactivity pharmacokinetic profiles are observed with tracer uptake, maximum and washout phases over the course of 5 hours. The EAAT2 density rich thalamus, frontal cortex and hippocampus regions with the high tracer 2 activities are thought indicative of EAAT2 interactions, based upon the findings from Examples V and VII, and also when compared to known high EAAT2 densities in these same primate cerebral regions determined by other means (Danbolt). Thus with the tracers of the invention, EAAT2 is detected in primate brain, including discrete cerebral ROIs with various known EAAT2 density distributions in the central nervous system, and the tracers are characterized with unique pharmacokinetic profiles for the detection of EAAT2.

All Embodiments

All publications and patent applications cited in this specification are hereby incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Other embodiments are within the claims.

What is claimed is:

1. A compound represented by

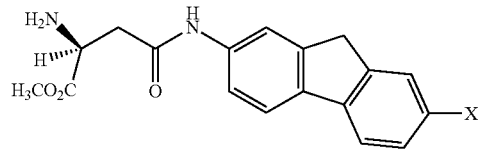

or a salt thereof,
wherein said compound is capable of crossing the blood-brain barrier and undergoing hydrolysis to yield an inhibitory radioligand that binds to excitatory amino acid transport protein 2.

2. The compound of claim 1, with a specific activity of at least 2.4 Ci/mmol.

3. The compound of claim 1 in combination with a pharmaceutically acceptable excipient.

4. A method of synthesizing a tracer compound represented by

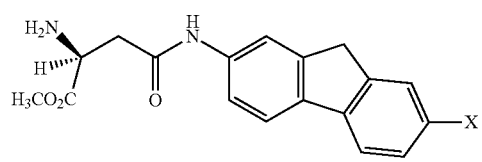

or a salt thereof, comprising the steps of
reacting 2-amino-7-iodofluorene with bis(triaklytin) in the presence of palladium catalyst to yield 2-amino-7-triaklystannyl-fluorene;
reacting said 2-amino-7-triaklystannyl-fluorene with a N-CBz O-methylester protected L-apsartic acid fragment in the presence EDC-HCl to yield a precursor adduct;
exposing said precursor adduct to [$^{18}$F]F$_2$ gas in liquid Freon; and
reacting the resulting product with HBr to yield said tracer compound, wherein said compound is capable of crossing the blood-brain barrier and undergoing hydrolysis to yield an inhibitory radioligand that binds to excitatory amino acid transport protein 2.

5. A method of detecting excitatory amino acid transport protein 2 comprising the steps of administering to a subject a compound represented by

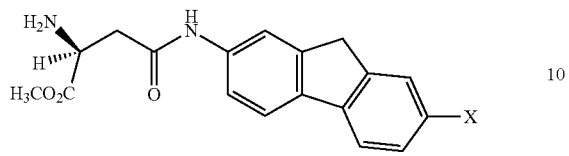

or a salt thereof, wherein said compound is capable of crossing the blood-brain barrier and undergoing hydrolysis to yield an inhibitory radioligand that binds to excitatory amino acid transport protein 2; and detecting said compound with a radiographic scanner.

6. The method of claim 5, wherein said radiographic scanner is a positron emission tomography scanner.

7. The method of claim 5, wherein said compound has a specific activity of at least 2.4 Ci/mmol.

8. The method of claim 5, wherein said subject is a human.

* * * * *